United States Patent
Dunn et al.

[19]

[11] Patent Number: 5,901,717
[45] Date of Patent: *May 11, 1999

[54] LIQUID WASTE DISPOSAL AND CANISTER FLUSHING SYSTEM AND METHOD

[75] Inventors: James L. Dunn; Timothy A. Carty, both of Topeka, Kans.

[73] Assignee: Dornoch Medical Systems, Inc., Riverside, Mo.

[*] Notice: This patent is subject to a terminal disclaimer.

[21] Appl. No.: 08/972,879

[22] Filed: Nov. 18, 1997

Related U.S. Application Data

[63] Continuation-in-part of application No. 08/848,576, Apr. 28, 1997, which is a continuation-in-part of application No. 08/698,940, Aug. 16, 1996, Pat. No. 5,776,260.

[51] Int. Cl.$^6$ ....................................................... B08B 9/08
[52] U.S. Cl. .................. 134/56 R; 134/57 R; 134/58 R; 134/116; 134/166 R; 134/169 R; 134/177; 134/186
[58] Field of Search .................................. 134/18, 24, 26, 134/56 R, 57 R, 58 R, 166 R, 177, 135, 104.2, 116, 150, 167 R, 168 R, 109 R, 22.12, 22.18, 186

[56] References Cited

U.S. PATENT DOCUMENTS

| | | |
|---|---|---|
| 1,693,885 | 12/1928 | Butterworth . |
| 1,827,085 | 10/1931 | Huff . |
| 2,370,775 | 3/1945 | Capita ........................ 134/24 |
| 2,641,270 | 6/1953 | Allen . |
| 2,896,643 | 7/1959 | Ottoson .................... 134/113 |
| 3,078,861 | 2/1963 | Miller ....................... 134/170 |
| 3,122,151 | 2/1964 | Chambers ................. 134/170 |
| 3,603,328 | 9/1971 | Fenn . |
| 3,780,757 | 12/1973 | Jordan . |
| 3,791,394 | 2/1974 | Hammelmann . |
| 3,897,599 | 8/1975 | Artzer . |
| 4,058,412 | 11/1977 | Knapp . |
| 4,905,325 | 3/1990 | Colditz . |
| 4,961,440 | 10/1990 | Wright . |
| 5,186,195 | 2/1993 | Wall . |
| 5,460,193 | 10/1995 | Levallois et al. . |

FOREIGN PATENT DOCUMENTS 650678  3/1979  Russian Federation .

*Primary Examiner*—Frankie L. Stinson
*Attorney, Agent, or Firm*—Rudnick & Wolfe

[57] ABSTRACT

A liquid waste disposal and canister flushing system includes a cabinet with a sink for receiving the canister and a subsink for receiving a lower portion thereof. The subsink is connected to a drain line. A plunger subassembly includes a stopper which functions as a drain valve for the canister. An injection jet is connected to water and cleaning solution sources and discharges diluted cleaning solution into the canister for flushing same. The injection jet engages the plunger subassembly for ejecting the stopper from a canister drain opening. A control system includes a programmable microprocessor which can be programmed to provide drain and flush cycles of predetermined duration. A number of different container and accessory embodiments are disclosed. A method of liquid waste disposal and canister flushing utilizes the microprocessor for delaying the flush cycle until completion of the drain cycle. The control system can provide drain and flush cycles of predetermined durations, can monitor water pressure, flow rate and temperature, cleaning solution flow rate, holding tank neutralizer inputs and timing and other system parameters.

21 Claims, 20 Drawing Sheets

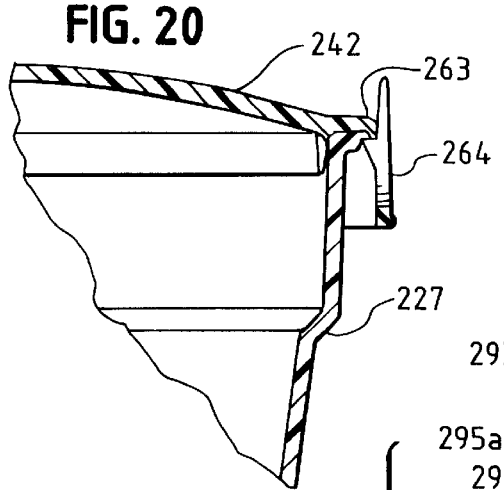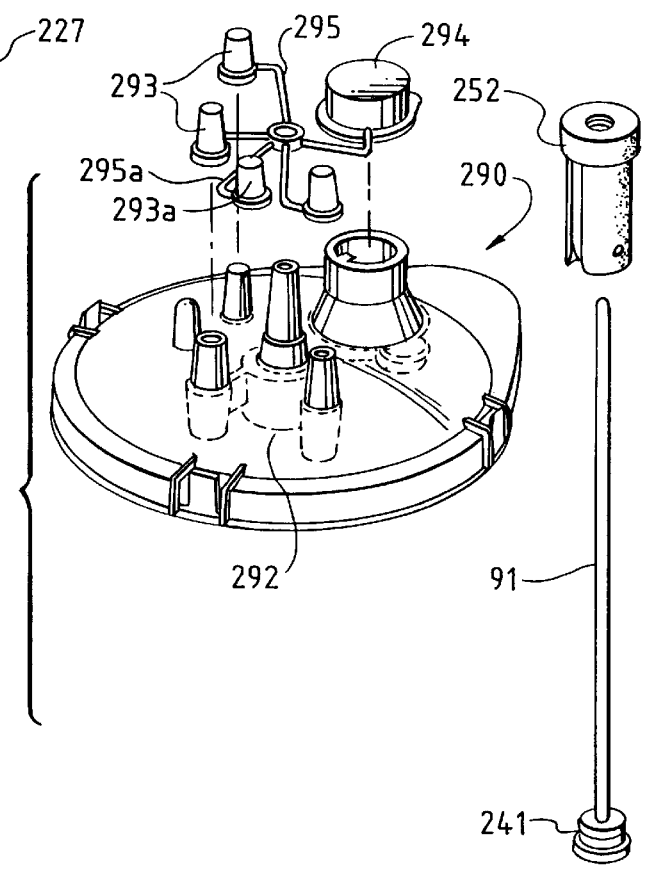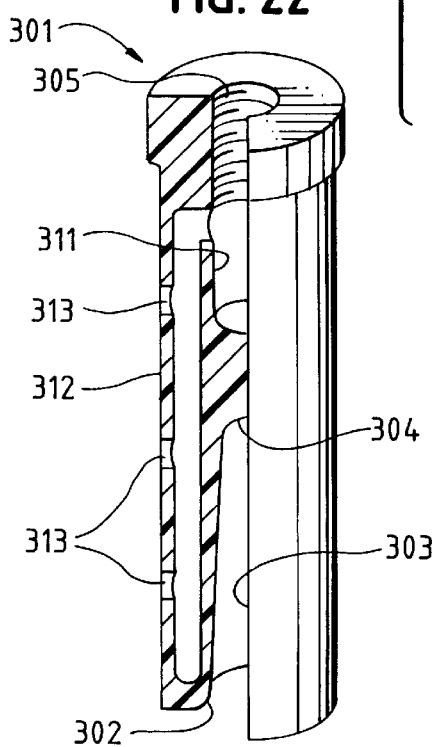

5,901,717

LIQUID WASTE DISPOSAL AND CANISTER FLUSHING SYSTEM AND METHOD

CROSS REFERENCE TO RELATED APPLICATIONS

This application is a continuation-in-part of application Ser. No. 08/848,576, entitled LIQUID MEDICAL WASTE DISPOSAL AND CANISTER FLUSHING SYSTEM AND METHOD, filed Apr. 28, 1997, still pending, which is a continuation-in-part of application Ser. No. 08/698,940, entitled LIQUID MEDICAL WASTE DISPOSAL AND CANISTER FLUSHING SYSTEM AND METHOD, filed Aug. 16, 1996 now U.S. Pat. No. 5,776,260.

BACKGROUND OF THE INVENTION

I. Field of the Invention

The present invention relates generally to liquid waste disposal and canister flushing, and in particular to the disposal of liquid medical waste from containers which are flushed in preparation for reuse and for disposable kits which adapt the reusable containers for flushing.

II. Description of the Related Art

Various forms of liquid waste are commonly encountered in a variety of different situations. For (example, liquid medical wastes are commonly produced in surgery and other medical procedures. Such wastes can include blood and other body fluids of patients, and major surgery can produce a number of containers of such waste from a single patient. Liquid medical waste generates significant disposal problems due to its possible contamination with various infectious diseases, including AIDS, hepatitis, MRSA and tuberculosis. In an effort to combat the risks associated with handling such liquid medical wastes and to protect medical personnel from the spread of infectious diseases, disposal procedures have become increasingly complicated and expensive.

One type of disposal procedure for liquid medical wastes involves emptying the waste canisters from surgery into specially designed plumbing fixtures. However, this procedure can involve risks associated with splash back and aerosolization whereby medical personnel can be exposed to the waste and bacteria present therein.

Another type of procedure involves the centralized collection of the waste with specially designed equipment having a liquid waste reservoir that must periodically be dumped. Such equipment is generally relatively expensive and can add significantly to the cost of equipping a hospital operating room or other treatment facility.

Yet another method of disposing of liquid medical waste involves mixing it with a solidifying agent in the container. The medical waste in the container then disposed of pursuant to regulations governing the disposal of bio-hazardous waste. The disadvantages with this disposal method include the cost of the canister, which becomes a single-use item, and the extra charges for disposing of bio-hazardous waste, which is sometimes referred to as "red bag" waste.

Liquid medical waste disposal procedures can come under rules and regulations imposed by various governmental and regulatory agencies, including the Occupational Safety and Health Administration (OSHA), the Food and Drug Administration (FDA), and the Center for Disease Control (CDC).

Heretofore there has not been available a liquid medical waste disposal system and method with the advantages and features of the present invention.

SUMMARY OF THE INVENTION

In the practice of the present invention, a liquid waste disposal and canister flushing system is provided which includes a cabinet forming a sink with one or more subsinks for receiving a bottom portion of a waste canister. The subsink(s) are connected to a drain line. In a first embodiment, each canister includes a lid with an accessory port, a base with a drain opening, and a sidewall connected to the lid and to the base. With a lower portion of the canister received in the subsink, the canister base is positioned above a bottom of the subsink. A plunger assembly includes a stopper positioned in the canister base drain opening for closing same and a rod with a lower end connected to the stopper and an upper end positioned in the canister lid accessory port. An injection jet is connected by water and cleaning solution lines to water and cleaning solution sources and mixes water and cleaning solution, such as bleach, to form a diluted cleaning solution which is discharged therefrom into the canister. The injection jet is inserted in the canister lid accessory port where it engages the plunger subassembly rod upper end and ejects the stopper into the subsink, thus opening the drain valve and permitting the liquid waste contents of the canister to drain into the subsink and then into the drain line. When the drain cycle is complete, the diluted cleaning solution is discharged from the injection jet into the canister for flushing same. A control system is provided for sequencing the drain and flush cycles whereby the flush cycle does not commence until the drain cycle is complete. The control system can include a programmable microprocessor which allows the drain and flush cycle durations to be adjusted, provides visual and audio indications of the status of the system in operation and which prevents flushing until the canisters are enclosed in the sink with a lid of the cabinet closed. Other functions which can be monitored and/or controlled by the microprocessor include water pressure for flushing, titration flow control of bleach to achieve desired cleaning solution/flush water ratios, monitoring of ratio of amount of liquid waste to volume of flush water, monitoring of water temperature, and storing and archiving of any exceptions to desired parameters and automatic shut-off of the system when parameters exceed a predetermined level. The cabinet can be equipped with lid locking solenoids to eliminate splash risk and the microprocessor can monitor the lid lock condition to prevent flushing operation when the lid is not locked down. An on-board modem can be provided for remote monitoring and emergency paging functions and an on-board LCD display can be provided for instantaneous feedback of system conditions.

A method of disposing of liquid waste and flushing a canister containing same is also provided and consists of the steps of draining the canister for a predetermined time prior to commencement of a flush cycle and flushing the canister for a predetermined time interval corresponding to a flush cycle.

In a first alternative form of canister, a reusable, rigid outer casing is used with a disposable flexible inner liner. The flexible liner, which is too flexible to be self-supporting, is preferably sonically welded to a lid with a plurality of upper openings, including an accessory port. The liner is also equipped with a bottom opening closed by a removable stopper and includes a plunger rod extending between the accessory port and the stopper. The rigid outer casing has a bottom opening, which can be closed by a stopper which is preferably manually removed prior to placement in the cabinet, and which is sized to rest partially in a subsink in the cabinet, as described above. The injection jet is then inserted into the accessory port, pushing the plunger rod downward to force the bottom stopper out of the liner. Any contents of the liner then drain out of the liner, out of the bottom opening in the casing and out of the subsink. Flushing and disinfecting is accomplished as described above. The flexible liner is disposable while the casing is reusable. The lid of the flexible liner, the outer casing, and, optionally, the subsink, can all be keyed such that a correct relative orientation is assured.

In a second alternative embodiment of canister, a semi-rigid container is provided whose composition resembles a plastic milk carton, i.e. it is rigid enough to be self supporting. As in the flexible liner, the semi-rigid container is also preferably sonically welded to a lid with a plurality of upper openings, including an accessory port. The liner is also equipped with a bottom opening closed by a removable stopper and includes a plunger rod extending between the accessory port and the stopper. While the semi-rigid liner can be positioned inside a rigid outer casing for transport, it is preferably designed for stand alone use with a special subsink in the cabinet. The special subsink has a perimeter wall which extends upward from the bottom of the sink and is sized to engage the lid of the semi-rigid container such that the subsink itself serves to support and surround the semi-rigid container during flushing and disinfecting operations. Again, as described above, once the semi-rigid container is in position in the subsink, the injection jet is inserted into the accessory port, pushing the plunger rod downward to force the bottom stopper out of the container. Any contents of the container then drain out of the container and out of the subsink. Flushing and disinfecting is accomplished as described above. The flushed and disinfected container can then be disposed of with ordinary refuse.

In a first alternative flushing arrangement, the bottom opening of the semi-rigid container can be eliminated and the internal plunger rod can have a sharp point, shaped as a trocar. When the plunger rod is forced downward by the flush jet, the trocar punctures the container bottom, thus allowing the fluid to drain therefrom. In a second alternative flushing arrangement, the internal plunger rod in the semi-rigid container can be eliminated and an upstanding plunger rod affixed to the bottom of the subsink, partially surrounding the subsink drain. The upstanding plunger rod can be equipped with a trocar point which punctures the bottom of the semi-rigid container when it is positioned in the subsink, thus causing it to drain. In either case, flushing and disinfecting are accomplished as described above, and the punctured semi-rigid container can be disposed of with ordinary refuse.

In either embodiment of flexible liner or semi-rigid container, the accessory port can be shaped as an inverted funnel, which acts as a guide for the internal plunger rod during insertion and draining operations. The bottom drain opening in the rigid containers and the flexible liners and semi-rigid containers can be filleted around the edges to eliminate sharp edges and to facilitate complete drainage. The accessory port can include an inside perimeter ridge which allows the flush jet to be snapped into position thereon.

In another embodiment of improved rigid container, the container includes a canister with a rim which is provided with an outwardly extending peripheral flange which mates with a similarly shaped outwardly extending peripheral receiver on a canister lid to key the lid or proper positioning on the canister. The accessory port in the lid includes a molded tab which extends inward into the opening and which mates with a slot on the flush jet to insure that the flush jet is properly oriented in the container. This insures that fluid from the flush jet hits the container wall at the desired position for optimum flushing conditions. The improved rigid container includes a bottom surface on the canister which has a gradual downward radius from the periphery to the center to insure that fluid does not pool on the container bottom when it is in an inverted position. The radiused canister bottom also includes a number of feet which are formed by molded ribs which extend downward from the radiused bottom with the ribs extending radially outward from the center of the container. The ribs insure that the canister sits stably on a flat surface and the canister drain opening is positioned between two of the ribs and elevated thereby so that a stopper can be placed in the drain opening without interfering with the canister stability.

Other improvements in the liquid waste disposal and canister flushing method and system include an improved tab locking system to lock the lid on the canister and a fail safe vacuum port fitting which insures that no vacuum can be drawn on the container from any port except the vacuum port. The canister drain opening stopper is provided with a peripheral ridge which acts as an O ring seal when the stopper is positioned in the canister drain opening. A single use disposable canister flush kit for use with the reusable canister includes a canister lid equipped with an integral Pour-X filter, a rod, drain plug and a plurality of canister lid port coverings attached together via links to form a spider-like shape. In a variation of flush jet port, the port is approximately doubled in length with a plurality of linked jet ports spaced along its lower half to optimally direct and divide the flush jet stream into the canister.

OBJECTS AND ADVANTAGES OF THE INVENTION

The principal objects and advantages of the present invention include: providing a liquid waste disposal and canister flushing system; providing such a system which facilitates the relatively inexpensive disposal of medical waste; providing such a system which facilitates reuse of medical waste containers; providing such a system which is relatively easily adapted for use with existing medical waste containers; providing such a system which reduces the splashing of medical waste being disposed; providing such a system which can reduce the hazards associated with handling and disposing of medical waste; providing such a system which facilitates the discharge of medical waste into a sewer system; providing such a system which can reduce the amount of disposable components associated with medical waste disposal; providing such a system which provides effective neutralization of various bacteria and infection sources; providing such a system which is usable by medical personnel with relatively little training; providing such a system with a control system which is at least partially automated; providing such a system which is relatively portable; providing such a system which is relatively compact; providing such a system which can be installed with relatively simple plumbing and electrical connections; providing such a system in which a jet port is keyed to the canister accessory port to optimize flushing; providing such a system with a canister with a tapered bottom which prevent fluid collection on the container bottom during inverted storage and cleaning; providing such a system in which a plurality of radial support ribs extend downward from the canister bottom to provide a stable support even with a stopper positioned in the canister drain opening; providing such a system with a single use kit which includes all elements needed to seal and flush a reusable canister; providing such a system which is economical to manufacture and use, efficient in operation, capable of a long operating life and generally well adapted for the proposed usage thereof; providing a liquid medical waste disposal and canister flushing method; providing such a method which is relatively efficient; providing such a method which is relatively safe; providing such a method which is relatively economical and providing such a method which is particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 20 is a greatly enlarged, fragmentary, cross-sectional view of a portion of the canister and canister lid of FIG. 16, illustrating a snap tab fitting between the lid and the canister peripheries.

FIG. 21 is an exploded assembly drawing illustrating a single use kit for flush adapting a reusable canister such as the canister of FIG. 16, including a disposable canister lid with a plurality of canister lid port coverings interconnected in a spider-like shape, a canister drain opening stopper and plunger.

FIG. 22 is a greatly enlarged perspective view of an alternative, longer jet port design with portions broken away to illustrate the interior construction thereof.

DETAILED DESCRIPTION OF THE INVENTION

Figure 1:
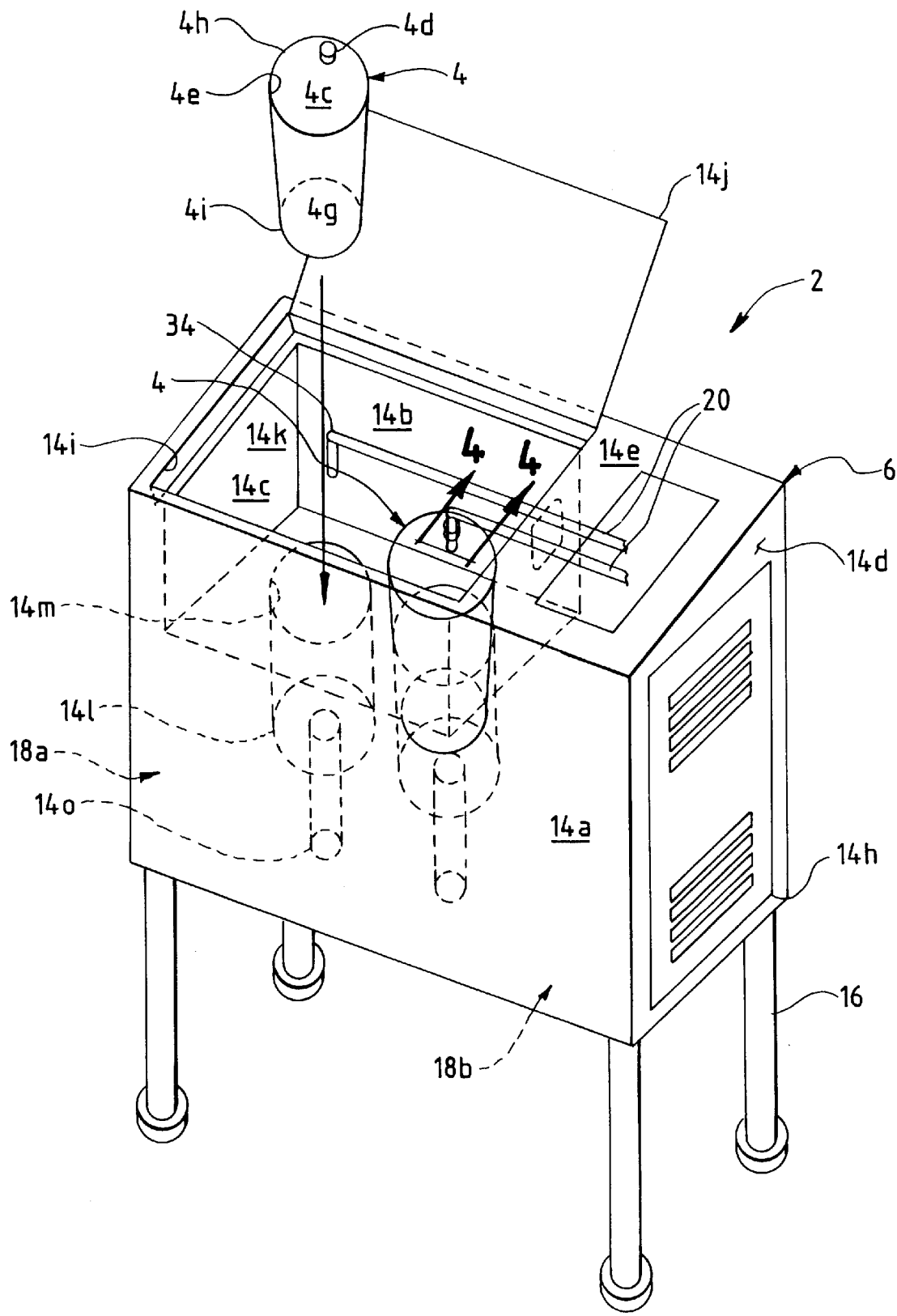
FIG. 1 is an upper, front perspective view of a liquid medical waste disposal and canister flushing system embodying the present invention.
Figure 2:
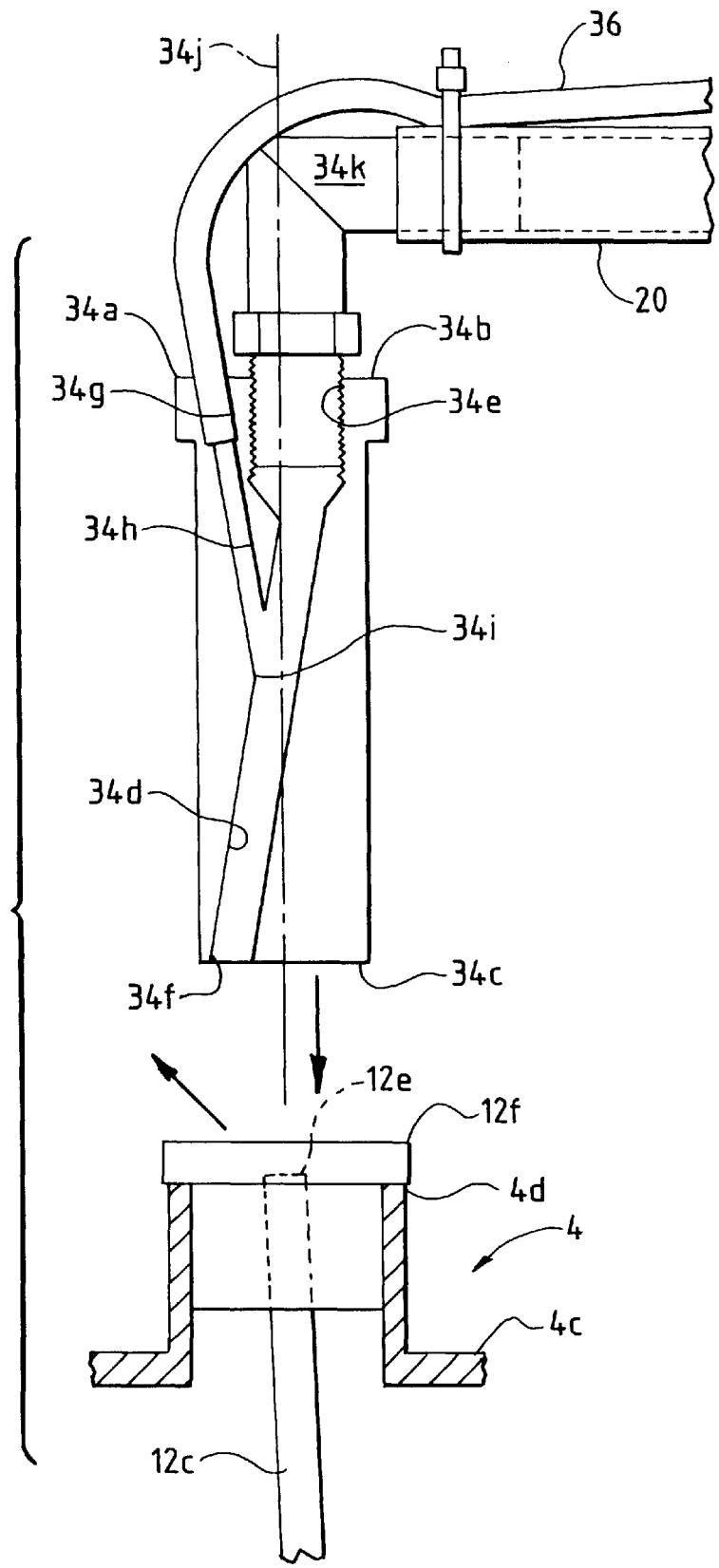
FIG. 2 is an enlarged, fragmentary, vertical cross-sectional view thereof.
Figure 3:
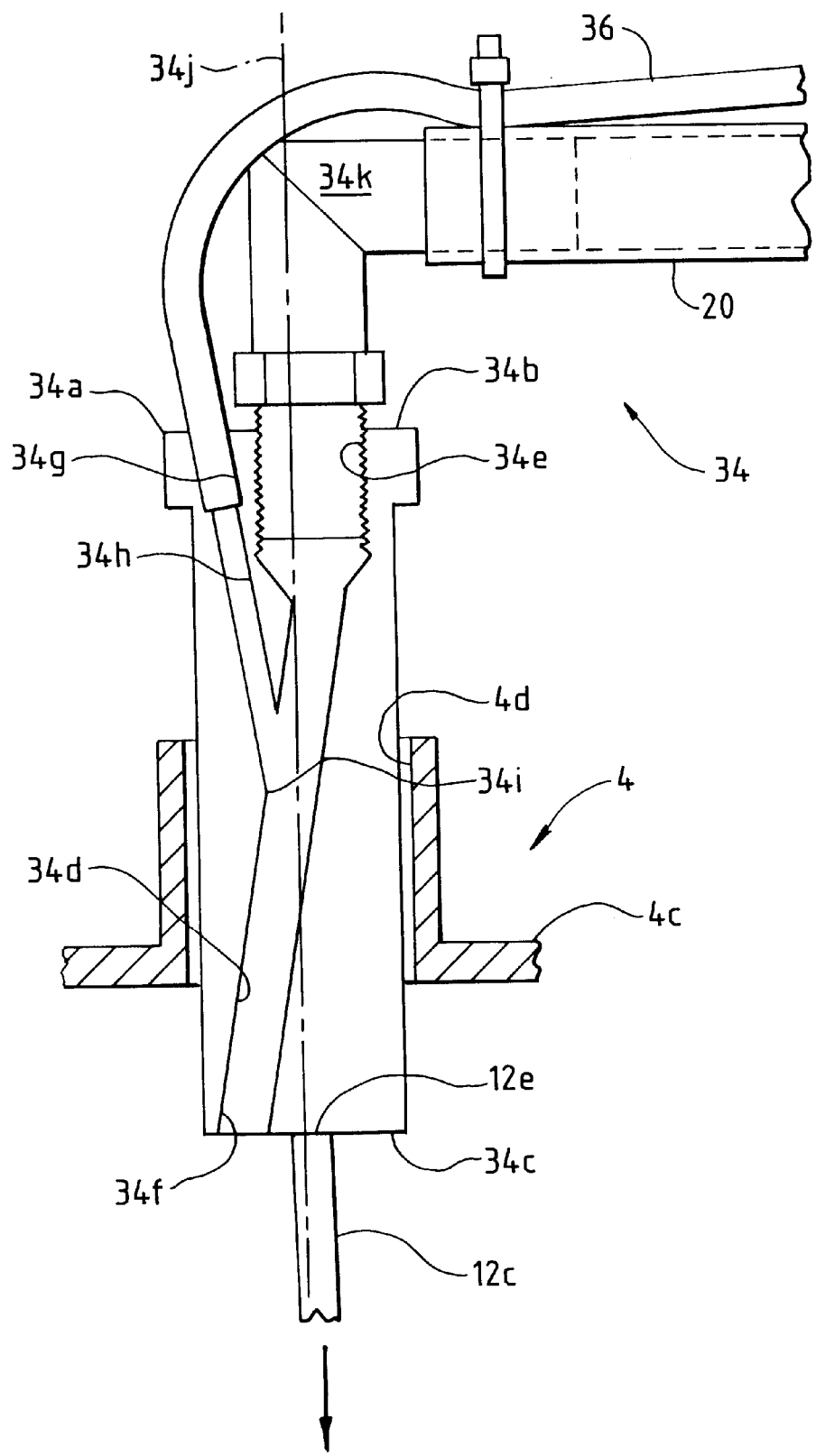
FIG. 3 is an enlarged, fragmentary, vertical cross-sectional view thereof, showing an injection jet being inserted into a canister lid and dislodging a plunger subassembly.
Figure 4:
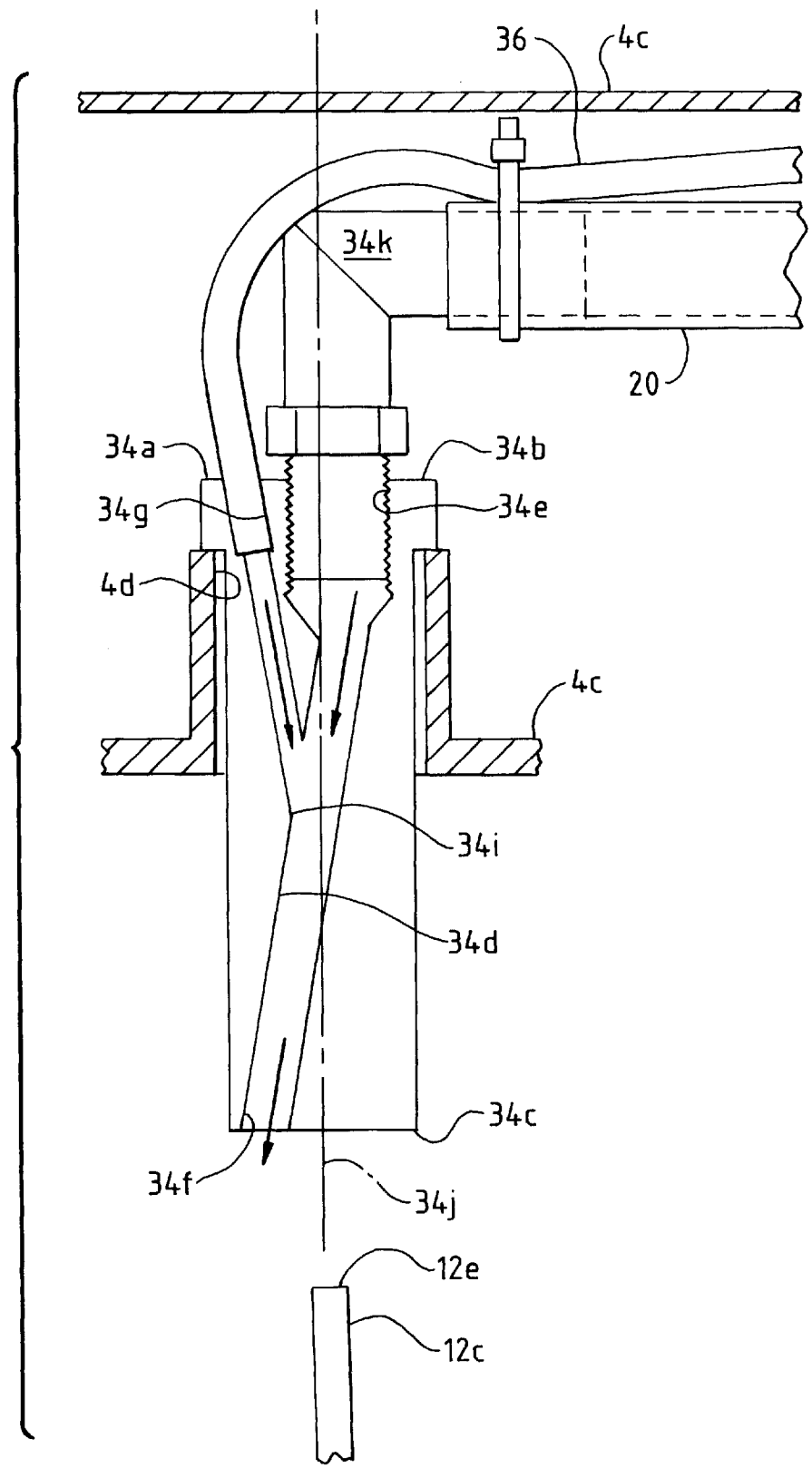
FIG. 4 is an enlarged, fragmentary, vertical cross-sectional view thereof, taken generally along line 4—4 in FIG. 1 and showing an injection jet inserted in the lid of one of the canisters.
Figure 5:
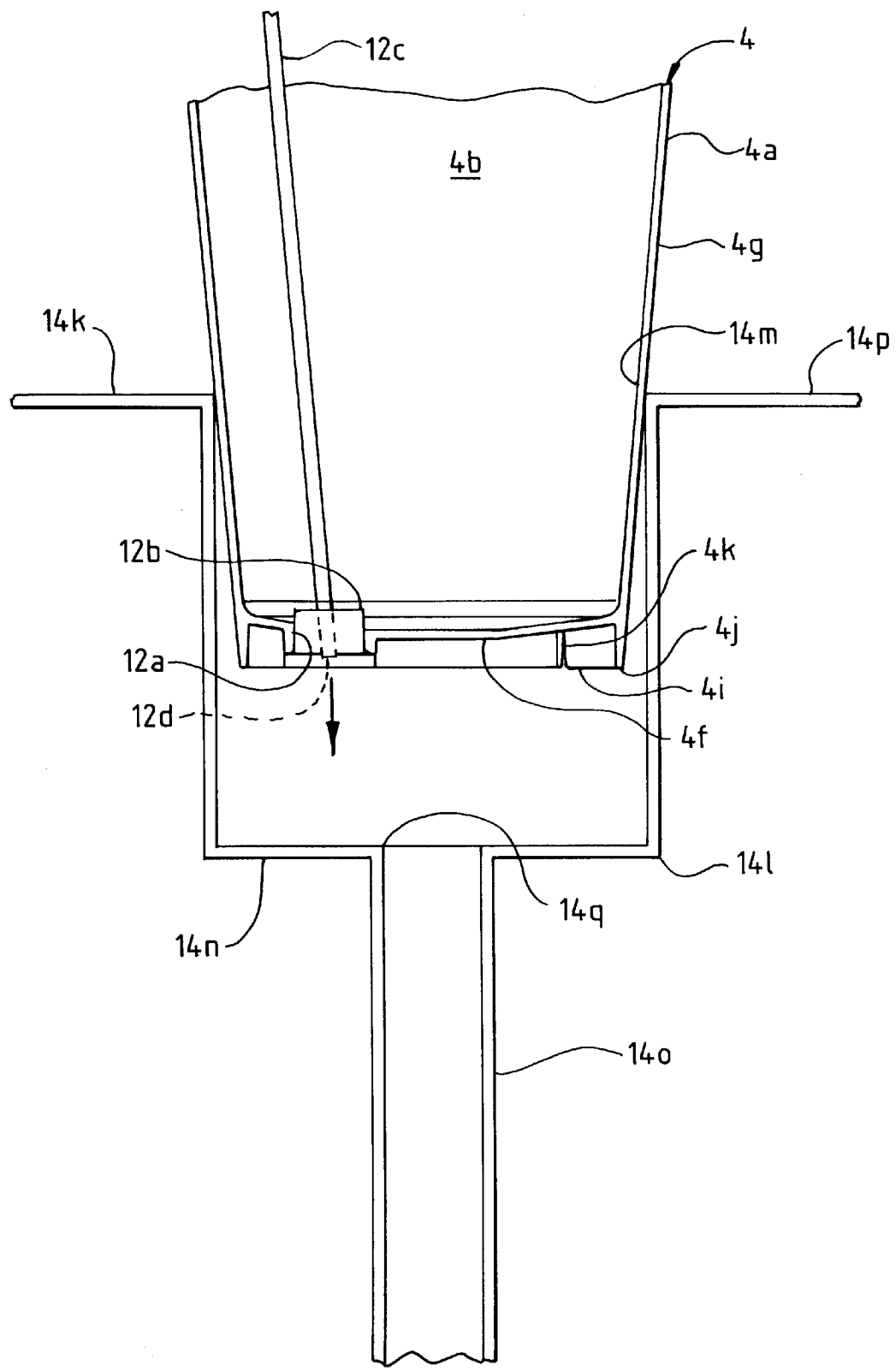
FIG. 5 is an enlarged, fragmentary, vertical cross-sectional view thereof, generally showing a lower end of the canister positioned in a subsink with the plunger subassembly in a closed position.
Figure 6:
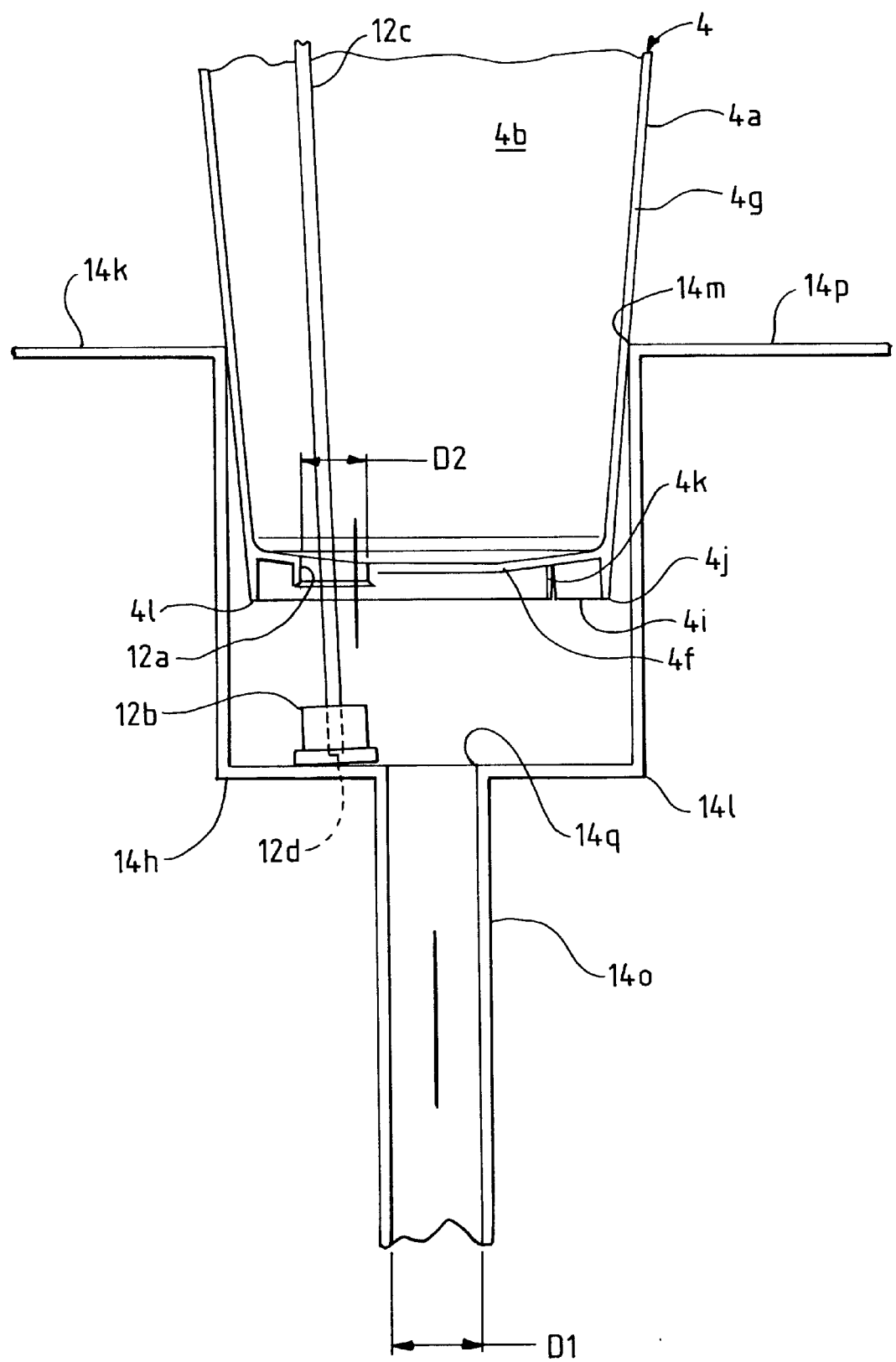
FIG. 6 is an enlarged, fragmentary, vertical cross-sectional view thereof, generally showing a plunger subassembly in an open, drain position.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 2 generally designates a liquid medical waste disposal and canister flushing system embodying the present invention. Without limitation on the generality of useful applications of the system 2, it is designed for operation on modified medical waste canisters 4. The system 2 generally comprises a cabinet 6, a plumbing system 8 and a control system 10.

II. Canister 4

An exemplary application of the disposal and flushing system 2 is with a canister 4 of the type which is commonly used in surgery for medical waste generally comprising the patient's blood and other fluids. A typical such canister is available from Allied Healthcare Products, Inc. of St. Louis, Mo. and includes a body 4a forming a container 4b of predetermined volume (e.g. 2550 milliliters) and a releasable lid 4c which is preferably upwardly-convex to prevent the pooling of fluids thereon. The body 4a includes upper and lower ends 4h,i. The lid 4c can be secured to the body 4a with a Leur lock-type connection and can include suitable inlet ports, fittings for vacuum lines, check valves, clamps, etc. The lid 4c includes an accessory port 4d with a generally cylindrical, tubular configuration and an open mouth 4e. The canister 4 further includes a base 4f, which is generally circular, and a frusto-conical sidewall 4g which converges downwardly in a tapering configuration to permit nesting of canister bodies 4a.

The canister 4 described thus far is a relatively standard configuration. For use with the system 2 of the present invention, the standard canister 4 is modified to include a plunger subassembly 12 for which a drain opening 12a is formed off-center in the canister base 4f and selectively receives a stopper 4b in sealing engagement. The canister base 4f is provided with a configuration which is concave from the inside of the canister and to facilitate drainage through the drain opening 12a, which opens at approximately the lowest level of the concave base 4f. A canister bottom flange or lip 4j extends downwardly from the canister base 4f and comprises an extension of the canister sidewall 4g. A plurality of drain notches 4k are formed in the bottom lip 4j and cooperate with the concave configuration of the canister base 4f whereby water will drain from the canister base 4f with the canister 4 in an inverted position, for example, when automatic dishwashing equipment is used for washing the canisters 4 in inverted positions.

A plunger rod 12c includes a lower end 12d embedded in the stopper 12b and an upper end 12e protruding into the accessory port 4d and mounting an upper cap 12f which is received in and is adapted to selectively close the accessory port 4d. In addition to the plunger subassembly 12 shown, other drain valve means can be utilized with the canister 4. These can include, for example, a variety of caps, lids, plugs and spring loaded devices for selectively opening and closing a drain opening formed in either the canister base 4f or the canister sidewall 4g.

III. Cabinet 6

The cabinet 6 includes front and back panels 14a,b; first and second side panels 14c,d; and a top 14e. The second side 14d has an opening which is selectively covered by a side access panel 14h. A top opening 14i is selectively covered by a lid 14j hingedly mounted on the top panel 14e. The top opening 14i provides access to a sink 14k. A pair of subsinks 14l with open, upper mouths 14m and subsink bottoms 14n depend downwardly from a floor 14p of the sink 14k. The subsinks 14l are generally cylindrical. Although two subsinks 14l are shown, the system 2 could include a single subsink 14l or more than two subsinks 14l. The subsinks 14l communicate through subsink drain openings 14q in their bottoms 14n with subsink drain lines 14o comprising the plumbing discharge subsystem 8b. The cabinet 6 is provided with adjustable-length legs 16 for leveling. An interior 18 of the cabinet 6 generally forms a sink chamber 18a and a control chamber 18b.

IV. Plumbing System 8

The plumbing system 8 generally includes a supply subsystem 8a and a drain subsystem 8b. The supply subsystem 8a includes a water inlet line 20 connected to a suitable pressurized water source 21, such as the normal municipal water service, a water tank or a water pump. A strainer 22 is provided in the water inlet line 20 and a backflow preventer valve 24 is provided downstream therefrom. The water inlet line 20 connects to a T-fitting 26, forming first and second supply branches 28a,b.

Each supply subsystem branch 28a,b includes a gate-type shut-off valve 30 and a solenoid-actuated valve 32 in line therewith. Each water inlet line 20 terminates in an injection jet 34, which also communicates with a cleaning solution injection line 36 communicating with a cleaning solution source 38, which can include a pump 39 for pumping the cleaning solution under pressure to the injection jet 34.

Each injection jet 34 includes a generally cylindrical body 34a with a flanged upper end 34b and a lower end 34c. A jet passage 34d extends downwardly from a threaded water inlet port 34e located off-center in the upper end 34b. The water inlet line 20 is connected to the water inlet port 34e by an elbow 34k. A discharge orifice 34f is located in the body lower end 34c, and is also off-center whereby the jet passage 34d is skewed with respect to a longitudinal axis 34j of the injection jet body 34a. Due to the skewed, angular orientation of the jet passage 34d, diluted cleaning solution therefrom is directed generally at the canister sidewall 4g, creating a swirling flushing action in the canister container 4b. A cleaning solution inlet port 34g is formed in the body upper end 34b and communicates with a cleaning solution passage 34h which forms a Y-intersection 34i with the jet passage 34d in an interior part of the body 34a. The cleaning solution inlet port 34g is connected to the cleaning solution line 36.

A venturi effect is created by passage of water through the jet passage 34d whereby cleaning solution is drawn through the cleaning solution passage 34h for combining with water to form the diluted cleaning solution mixture which is discharged through the discharge orifice 34f.

An optional clot-dissolving solution source 40 communicates with a drain line jet 42 directed into the drain line 14o and functions to dissolve blood clots therein. Although the clot-dissolving solution source 40 and the jet 42 are optionally shown on the second plumbing system branch 28b, they could be provided on the first branch 28a as well, or eliminated all together whereby clots in the drain line 14o could be dealt with manually.

V. Control System 10

The control system 10 utilizes a control microprocessor 50. A program port 52 provides input access to the microprocessor 50 through a suitable RAM device 53a. A ROM device 54 is also connected to the microprocessor 50.

Analog-to-digital input conversion capabilities are provided by an A\D convertor 56 which is connected to an encoder 58, which in turn is connected to the microprocessor 50 through a RAM device 53b. A selection key 60 also provides digital input to the encoder 58. A level probe 62 is connected to the solution source 38 for monitoring the level therein and is connected to the RAM device 53b through an amplifier 62a.

A solenoid valve control 64 includes a digital output module 64a which is connected to the solenoid valves 32 and to a pair of indicator lights 64b for indicating the open or closed positions of the solenoid valves 32. The digital output module 64a is connected to the microprocessor 50 through a RAM device 53c.

A display device 66 is mounted on the cabinet top panel 14e and is connected to the microprocessor 50 through a RAM device 53d and a driver 66a and can comprise, for example, an LED or LCD display for indicating the state of the control system 10 or various functions thereof, such as time remaining to complete a flush cycle, delay mode (as explained in more detail below), etc.

Figure 8:
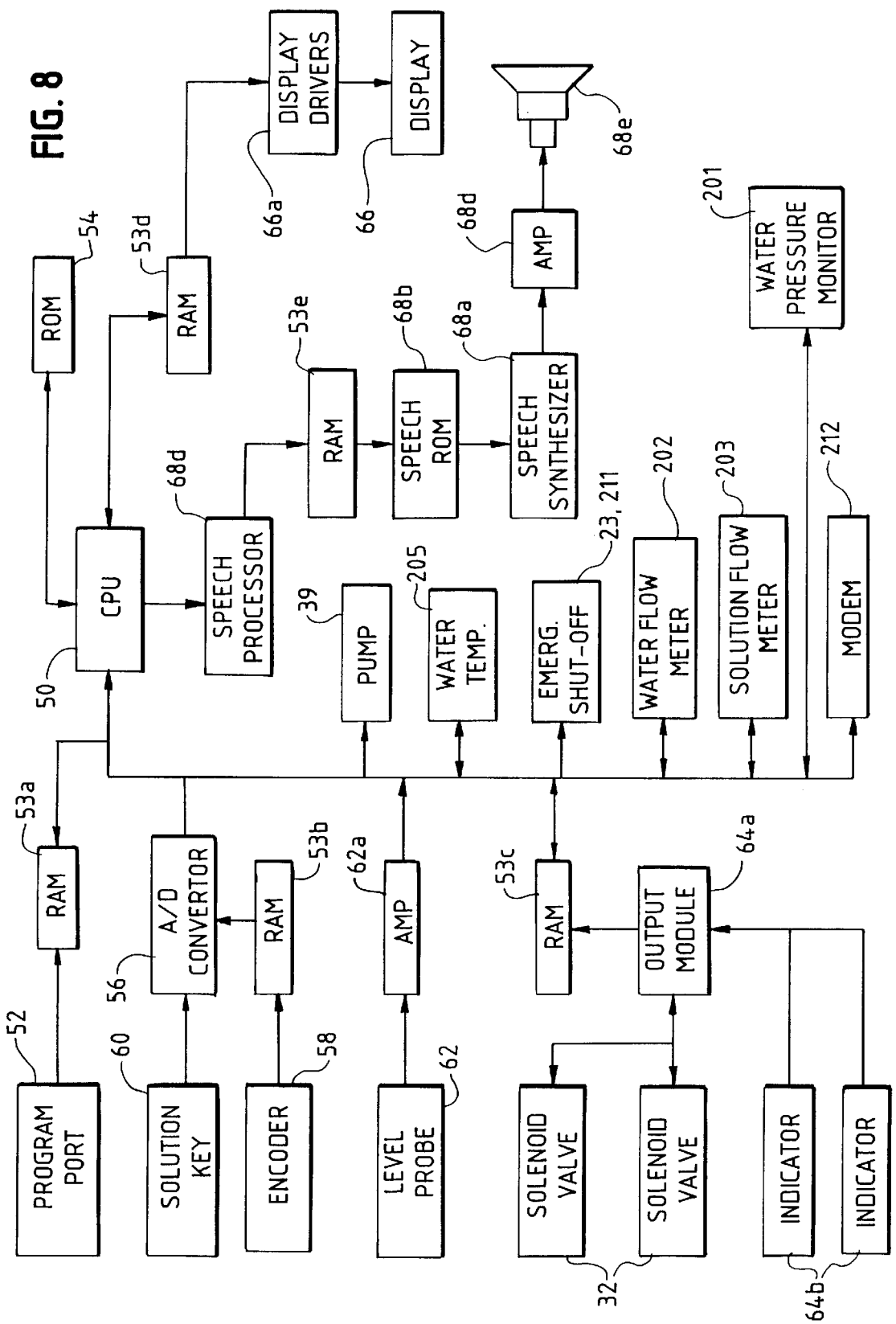
FIG. 8 is a schematic diagram of a control system thereof.

A voice enunciation subsystem 68 includes a speech synthesizer 68a connected to the microprocessor 50, a RAM device 53e, a speech ROM device 68b, an amplifier 68d and a suitable output device, such as a speaker 68e, all suitably interconnected as shown in FIG. 8. A water pressure sensor 201 is connected to the microprocessor 50 for monitoring water pressure to insure that it is adequate. A water flow sensor 202 and an additive flow sensor 203 monitor fluid flow to allow titration of the additive and flow of water to be monitored to calculate concentration of additive (cleaning solution) in the water. The microprocessor 50 thus controls valves 32 and the pump 39 to achieve the desired additive concentration. Monitoring of water flow by the microprocessor 50 insures compliance with government regulations. A water temperature monitor 205 allows the microprocessor 50 to monitoring of water temperature. A remotely controlled emergency shut-off 23 and 211 allows the microprocessor 50 to shut off the drain of the cabinet 6 as well as all fluid inputs in the event that monitored parameters are outside of predetermined limits. The microprocessor 50 also stores and archives of any exceptions to desired parameters. An optional modem 212 can be provided for remote monitoring and emergency paging functions for the on-board display 66 can be provided for instantaneous feedback of system conditions.

It will be appreciated that the control system 10 can comprise various alternative configurations with appropriate analog, digital or analog/digital components for controlling various functions of the system 2. In particular, other inputs and outputs could be provided for monitoring various functions of the system 2 and for automating same to a greater or lesser degree.

VI. First Alternative Embodiment of Canister 71

Figure 10:
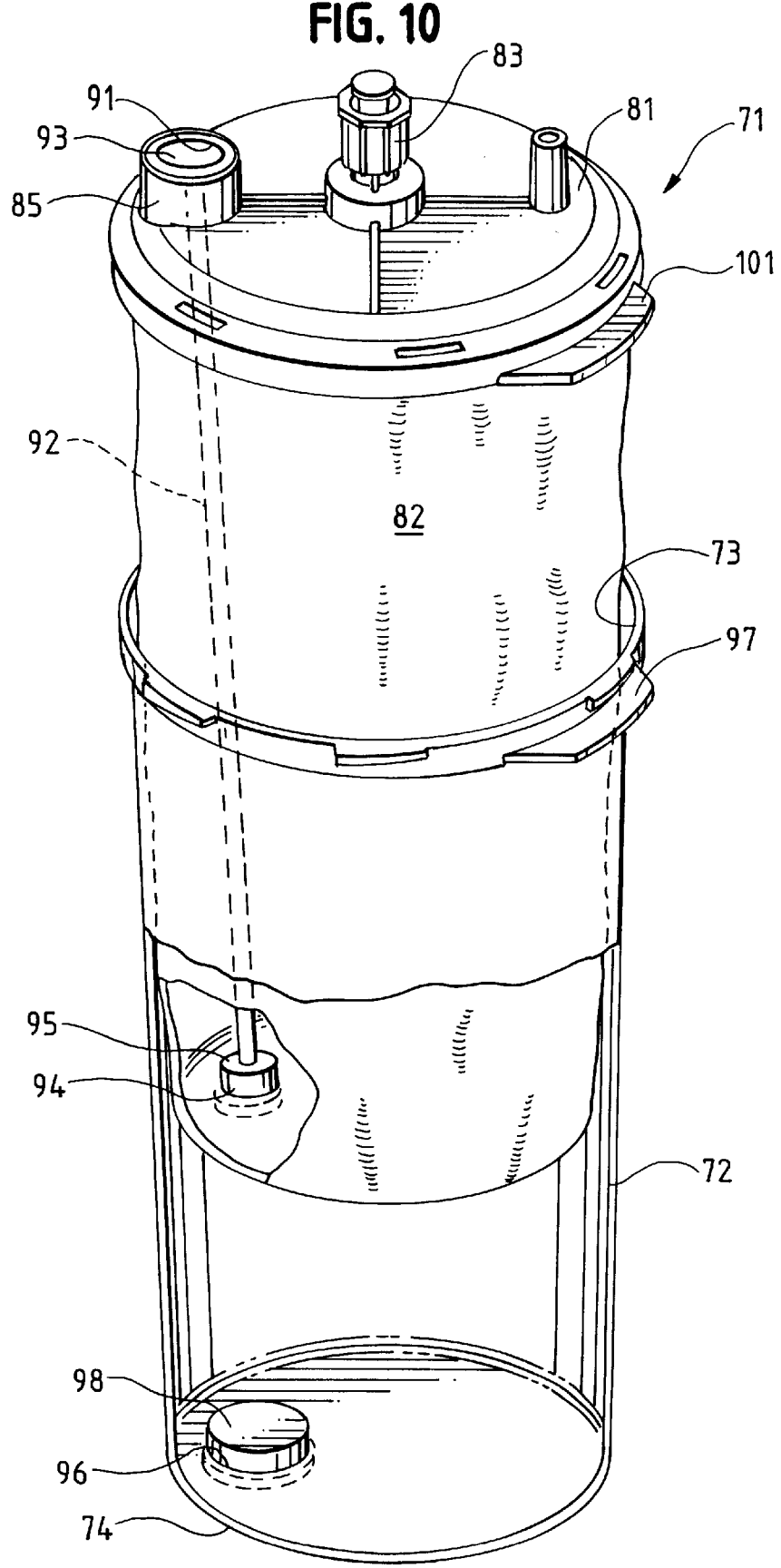
FIG. 10 is a perspective view of a first alternative embodiment of canister with disposable flexible liner.
Figure 11:
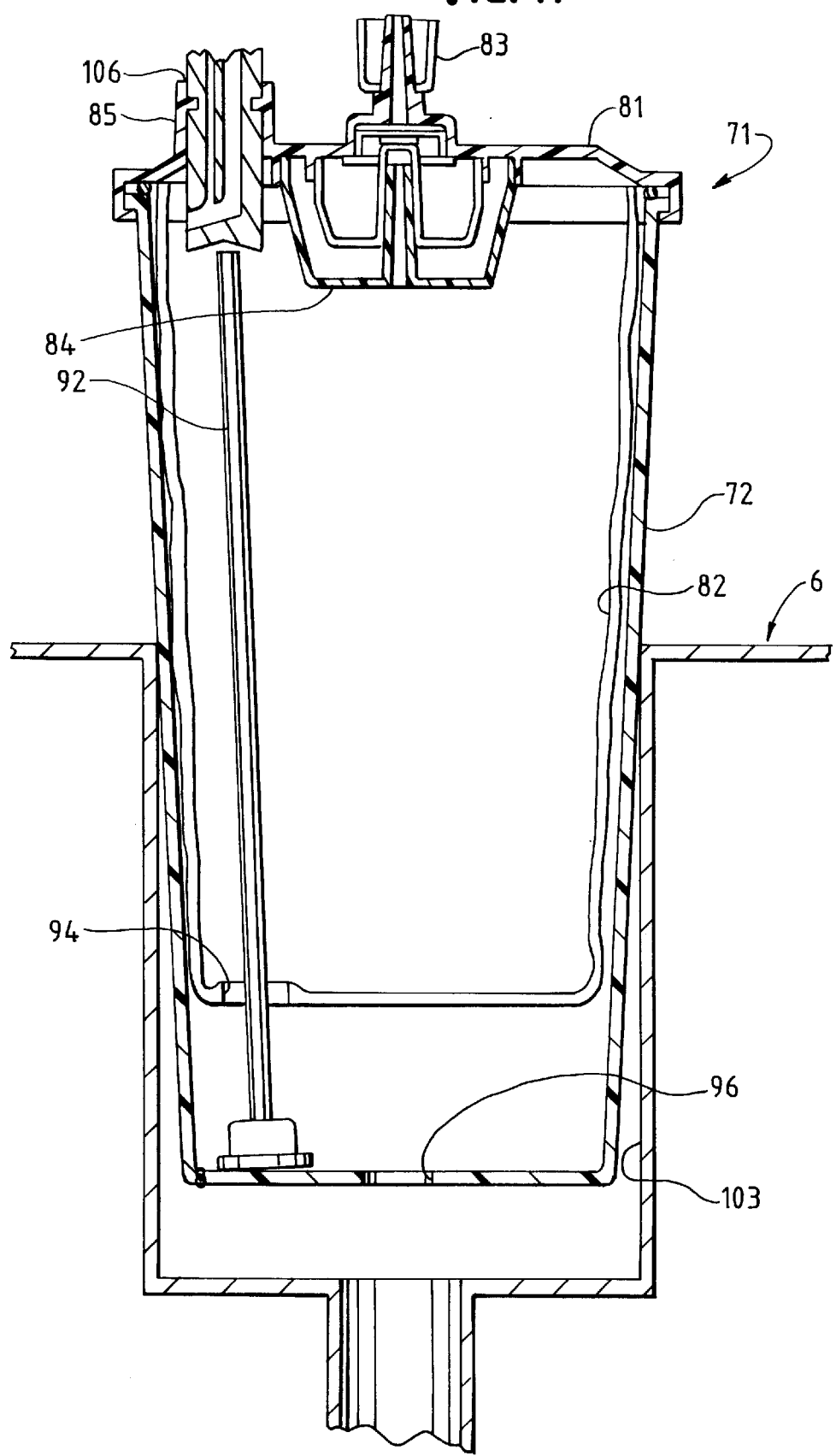
FIG. 11 is a cross-sectional view of the container of FIG. 10, positioned in a subsink in a cabinet and with a flush jet inserted into position for flushing and disinfecting.

Referring to FIGS. 10 and 11, a first alternative embodiment of canister is generally indicated at 71. The canister 71 includes a rigid outer casing 72 with perimeter walls which preferably form a frusto-conical shape extending from a generally circular open top 73 to a smaller diameter, generally circular closed bottom 74. The rigid casing 72 can be similar to the canister 4 described earlier, and can include a Leur lock-type connection 75 at the open top 73 to accommodate a releasable lid 81 which is, again, preferably upwardly-convex to prevent the pooling of fluids thereon. The lid 81 is sonically welded to a flexible liner 82 and includes a fitting 83 for a vacuum line with an internal check valve 84. The lid 81 also includes an accessory port 85 which opens into the interior of the flexible liner 82. The port 85 is shaped with generally cylindrical, tubular configuration, and can include at least one sloping wall 86 which resembles an inverted funnel, and an open mouth 91.

A plunger rod 92 is attached to a plug 93 which covers and seals the open mouth 91 of the port 85. The sloping wall 86 acts as a guide for the plunger rod as it is inserted into the liner 82. A drain opening 94 is formed in the bottom of the flexible liner 82, and the drain opening 94 can be reinforced to hold a removable stopper 95 which is engaged by the plunger rod 92. The closed bottom 74 of the rigid casing 72 includes a drain opening 96 which can be beneath (FIG. 10) or offset from (FIG. 11) the drain opening 94 in the flexible liner 82. In order to assure proper alignment of the liner 82 and the outer casing 72, an optional ovate key extension 97 can be included in the open top 73 of the casing 72, which key extension 97 mates with a similar, optional extension 101 in the lid 81 when the liner 82 is properly aligned in the casing 72. The bottom 74 of the casing 72 is preferably provided with a concave upper surface to facilitate drainage through the drain opening 95. An optional removable stopper 98 similar to the stopper 95 is positionable in the drain opening 96, which stopper 98 is preferably removed prior to insertion of the casing 71 in a subsink 103 of the cabinet 6, as shown in FIG. 11. The drain opening 95 can have filleted edges 99 to minimize sharp surfaces.

Figure 12:
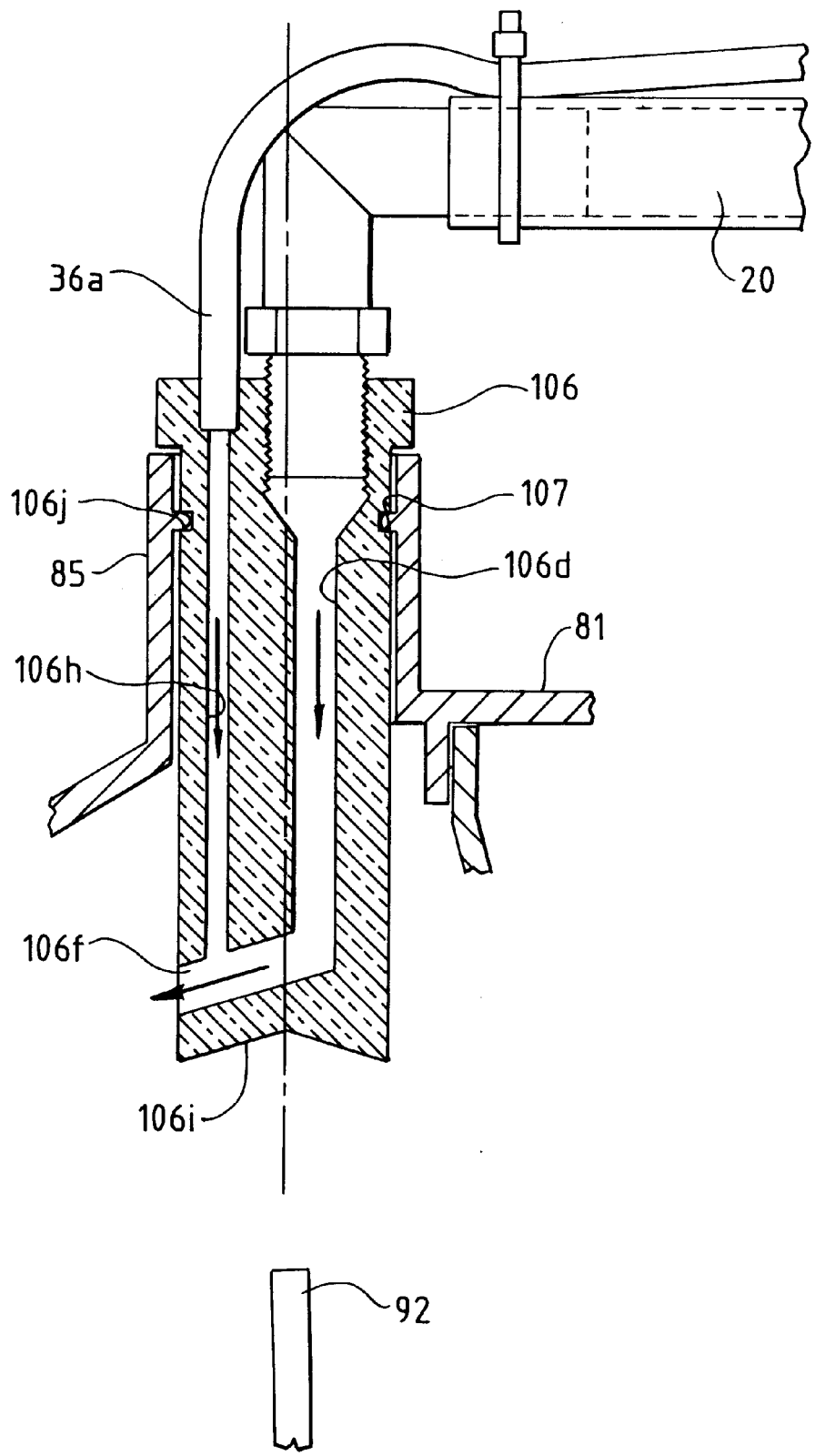
FIG. 12 is a greatly enlarged, cross sectional view of a modified flush jet fitting designed to eliminate any venturi effect between water inlet and cleaning solution inlet.

The port 85 serves as a receptacle for a modified injection jet 106 (best illustrated in FIG. 12), which also communicates with a cleaning solution injection line 36a. The modified jet 106 is designed to eliminate any venturi effects created by passage of water through a jet passage 106d whereby cleaning solution pressure and flow can be accurately controlled solely by operation of a disinfectant pump (not shown in FIG. 11) attached to the cleaning solution passage 106h for combining with water to form the diluted cleaning solution mixture which is discharged through a discharge orifice 106f. The injection jet 106 also includes a beveled bottom surface 106i which accommodates a top of the plunger rod 92 to securely hold the plunger rod 92 as it is being forced downward by the jet 106. Again, by introducing the jet 106 into the port 85, the plunger rod 92 pushes the stopper 95 out of the drain opening 94, thus draining the flexible liner 82 and preparing the liner 82 and the casing 72 for flushing and disinfectant. The injection jet 106 can incorporate a perimeter slot 106j which mates with an interior perimeter ridge 107 in the port 85 to securely snap the injection jet 106 into position within the port 85.

VII. Second Alternative Embodiment of Canister 111

Figure 13:
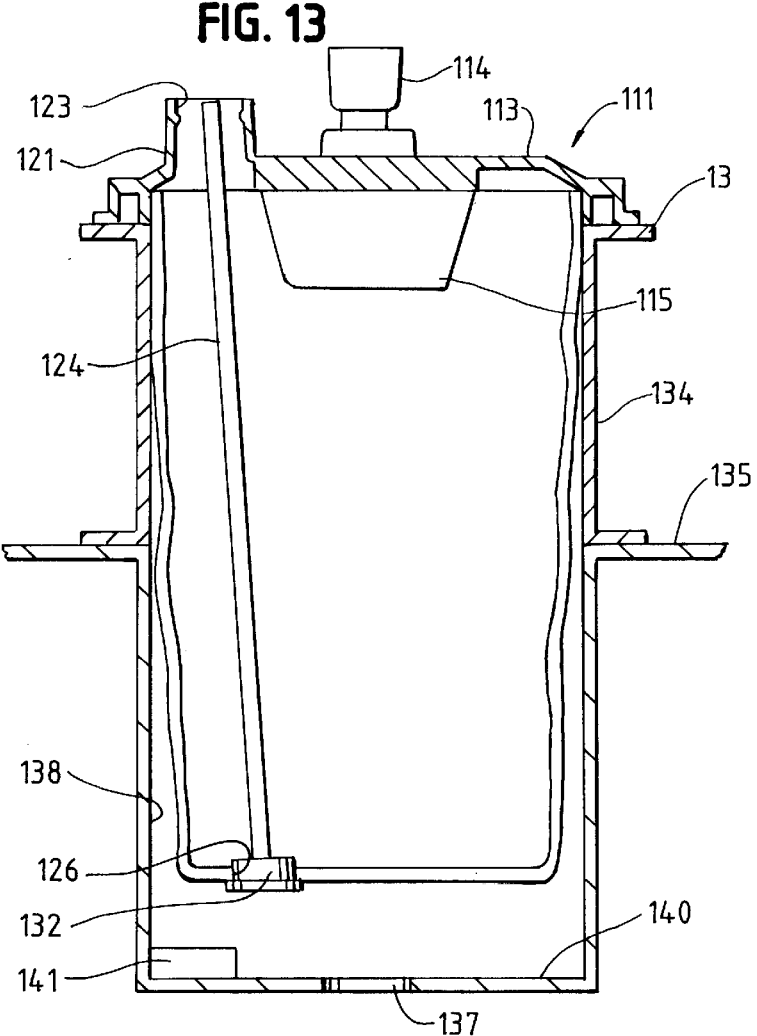
FIG. 13 is a cross-sectional view of a second embodiment of canister including a semi-rigid container with an internal plunger rod and bottom opening inserted into a modified subsink.

Referring to FIG. 13, a second alternative embodiment of canister is generally indicated at 111. The canister 111 comprises a semi-rigid container 112 which is preferably sonically welded to a lid 113. The lid 113 is similar to the lid 81, i.e. it is preferably upwardly-convex to prevent the pooling of fluids thereon and includes a fitting 114 for a vacuum line with an internal check valve 115. The lid 113 also includes an accessory port 121 which opens into the interior of the semi-rigid container 112. The port 121 is shaped with generally cylindrical, tubular configuration and an open mouth 123.

A plunger rod 124 is attached to a stopper 125 which covers and seals the open mouth 123 of the port 121. A drain opening 126 is formed in a bottom 131 of the semi-rigid container 112, and the drain opening 126 can be reinforced to hold a removable stopper 132 which is engaged by the plunger rod 124.

The canister 111 is designed to work with a modified subsink 133 which includes a cylindrical perimeter wall 134 which extends upward from a bottom surface 135 of the sink chamber 18a of the cabinet 6. The lid 113 has peripheral ledge which is sized to rest on an upper surface 136 of the subsink perimeter wall 134 in a position such that the drain opening 126 in the semi-rigid container 112 is positioned above a bottom surface 140 of the subsink 133. In order to minimize "swirl" of the drained contents of the container 112 in the bottom of the subsink 133, a swirl stop 141 can be positioned on the bottom surface 140. The swirl stop 141 is simply a narrow rectangular block which has a bottom surface adhered to the bottom surface 140 and a side surface adhered to a lower perimeter wall 138 of the subsink 133 such that it interferes with any swirling action of fluid in the subsink 133 to enhance the draining action of the fluid through a centered drain opening 137.

As in the canisters 4 and 71, the port 121 serves as a receptacle for the injection jet 34 or 106 (not shown), for purposes described above. By introducing the jet 34 or 106 into the port 121, the plunger rod 124 pushes the stopper 132 out of the drain opening 126, thus draining the semi-rigid container 112 and preparing it for flushing and disinfectant.

Figure 14:
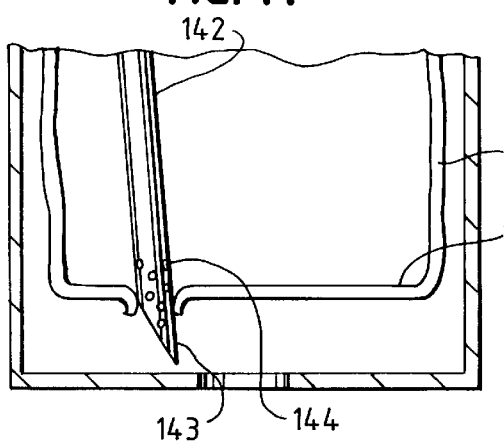
FIG. 14 is a fragmentary, cross-sectional view of a modified version of semi-rigid container, including an internal plunger rod with a sharp point designed to puncture the container bottom from within upon insertion of a flush jet.

Referring to FIG. 14, an alternative version of plunger rod 142 is illustrated for use with a modified semi-rigid container 112a. The container 112a is similar in all respects to the container 112, except that it is equipped a continuous bottom 131 a with no openings. The plunger rod 142 includes a sharp, trocar-like point 143 on the bottom end thereof, which point 143 is designed to puncture the bottom 131 a of the semi-rigid container 112a when engaged by the jet 34 or 106 being introduced into the port 121. Any liquid in the container 112a is thus allowed to drain out through the punctured bottom 131a. The plunger rod 142 can be hollow with openings 144 in the perimeter thereof to facilitate drainage of the container 112a.

Figure 15:
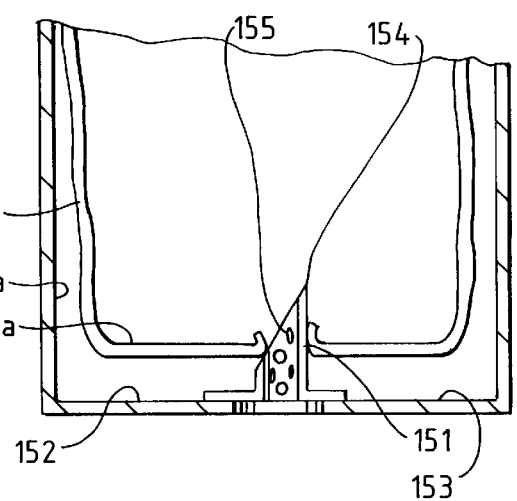
FIG. 15 is a fragmentary, cross-sectional view of another modified version of semi-rigid container, including an internal plunger rod extending upward from around the drain opening of the subsink and also equipped with a sharp point designed to puncture the container bottom from without once the container is properly seated in the subsink.

Referring to FIG. 15, a second alternative version of plunger rod 151 is illustrated for use with the modified semi-rigid container 112a. Again, the container 112a is similar in all respects to the container 112, except that it is equipped a continuous bottom 131 a with no openings. The plunger rod 151 is attached to and extends upward from a bottom surface 152 of a modified subsink 133a, preferably in surrounding relationship with a subsink drain opening 153. The plunger rod 151 also includes a sharp, trocar-like point 154 on the top end thereof, which point 154 is designed to puncture the bottom 131 a of the semi-rigid container 112a when it is properly positioned on the upstanding perimeter wall 134 of the subsink 133a, as described above and illustrated in FIG. 13. All liquid waste in the container 112a is thus allowed to drain out through the punctured bottom 131a. Again, the plunger rod 151 can be hollow with openings 155 in the perimeter thereof to facilitate drainage of the subsink 133a.

VIII. Third Alternative Embodiment of Canister 221

Figure 16:
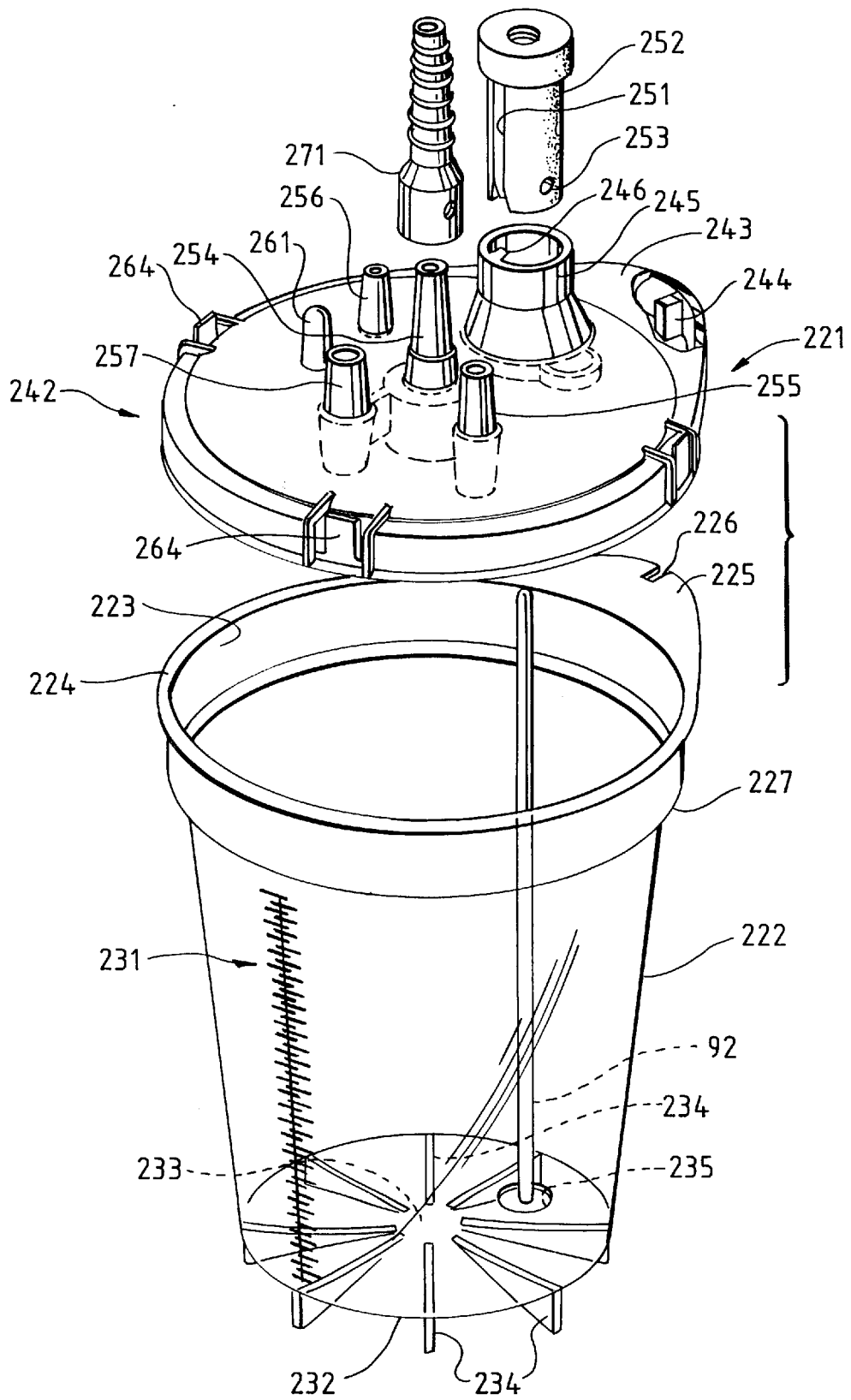
FIG. 16 is a perspective view of an alternative rigid canister with a canister lid shown removed from and positioned above a canister with a drain plug and plunger positioned in the canister and with a keyed jet port and an inventive vacuum adapter fitting positioned above the canister lid.
Figure 17:
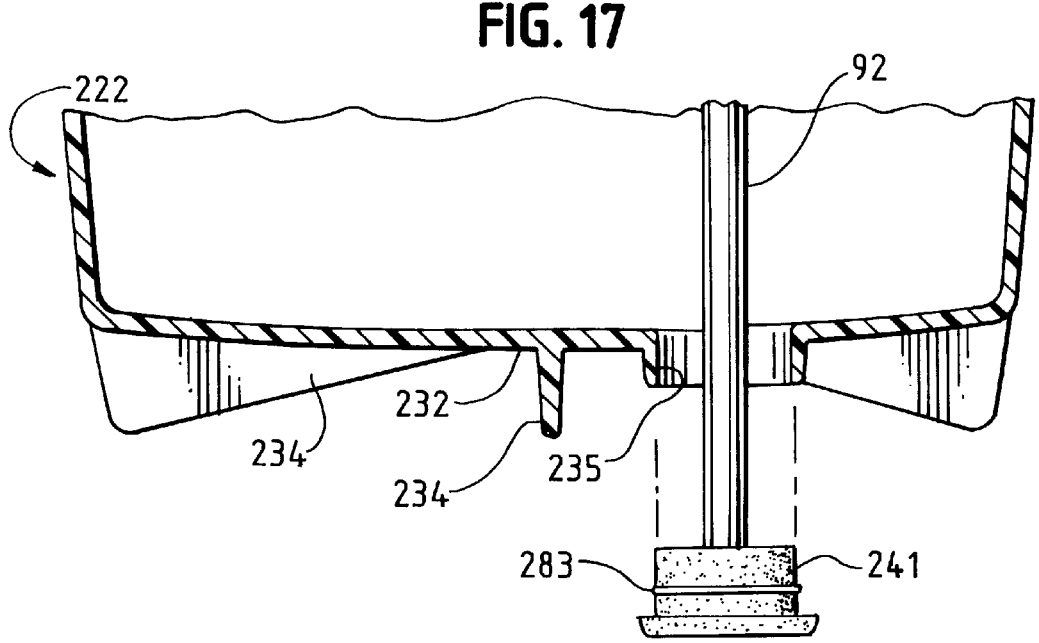
FIG. 17 is an enlarged, fragmentary, cross-sectional view of a lower portion if the canister, showing the radiused bottom with a plurality of radial support ribs extending downward therefrom and with a drain stopper equipped with a radial peripheral ridge.

Another embodiment of rigid canister and associated flushing equipment is illustrated in FIGS. 16, 17 and 20, and generally indicated at 221. The canister 221 includes a container 222 with a truncated, generally frusto-conical shape. The container 222 has an open top 223 surrounded by a rim 224, a portion of which extends outwardly to form a peripheral flange 225 with a centered slot 226 formed therein. The sidewall of the container 222 tapers sharply inward to from a ledge 227 such that the ledge 227 of the container 222 rests on the top lip of a subsink, such as the subsink 133. The container 222 preferably has graduated scale indicia markings 231 and has a bottom surface 232 which is gradually radiused downward (FIG. 16) from the container periphery inward to a center portion 233 to insure that fluid does not pool on the container bottom surface 232 when it is in an inverted storage position (not shown). Extending downward from the radiused container bottom 232 are a number of feet 234 which are formed by molded ribs which extend radially outward from the center to the periphery of the container 222. The feet 234 insure that the container 222 sits stably on a flat surface and a container drain opening 235 is positioned between two of the feet 234 and is thus elevated thereby so that a stopper 241 can be placed in the drain opening 235 without interfering with the stability of the container 222.

The canister 221 also includes a container lid 242 which is generally circular, but which includes an outwardly extending peripheral receiver portion 243 which is shaped and sized to mate with the peripheral flange 225 on the container 222 and which has a tab 244 extending inward from an outer periphery thereof which is positioned within the slot 226 when the lid 242 is correctly placed on the container 222. The combination of the flange 225 and slot 226 and the receiver portion 243 and tab 244 act as a key to insure that the lid 242 is properly positioned on the container 222 such that the container drain opening 235 is aligned with an accessory port 245 on the container lid 242. The accessory port 245 is shaped as an inverted funnel and includes a molded tab 246 which extends inward into the accessory port 245 and which mates with a slot 251 on a flush jet adapter 252 to insure that a port 253 in the flush jet adapter 252 is properly oriented in the canister 221. This insures that cleaning fluid from the flush jet adapter port 253 hits the interior of the container 222 at a desired position to create a tornadic cleaning motion of the fluid within the container 222 for optimum flushing conditions. The lid 242 is also equipped with a centered vacuum supply port 254, a patient port 255, a tandem port 256, an ortho port 257 and a tube plug 261.

Referring to FIG. 20, the container rim 224 includes a peripheral lip 263 which mates with a plurality of resilient tabs 264 which are integrally molded into the container lid 242. As the container lid 242 is lowered into position atop the container 222, the tabs snap under the lip 263 to securely hold the lid 242 in place. There are at least four of the tabs 264 positioned about the periphery of the lid 242 and removal of the lid 242 requires that an adjacent pair of the tabs 264 be pulled backward while the lid 242 is simultaneously lifted and then a third tab 264 must be pulled backward to release the lid 242. The inventive tab locking system is designed to prevent inadvertent contact with effluents within the canister 221.

IX. Fail Safe Vacuum Port Adapter 271

Figure 18:
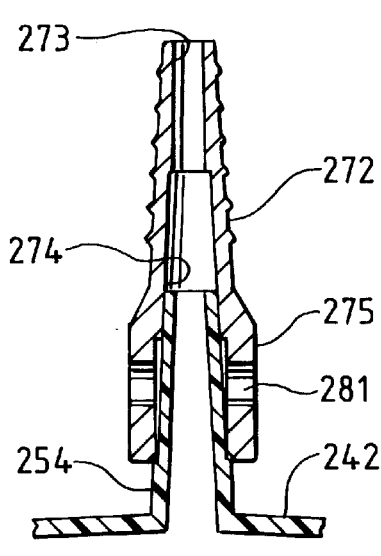
FIG. 18 is a greatly enlarged, fragmentary, cross-sectional view of a non-vacuum port on the canister lid of FIG. 17, with the inventive vacuum adapter fitting being prevented from sealing off the port.
Figure 19:
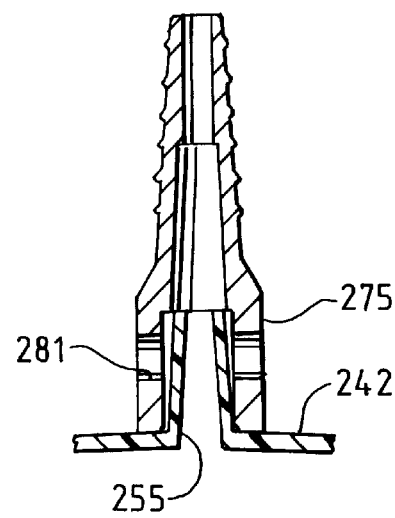
FIG. 19 is a greatly enlarged, fragmentary, cross-sectional view of a vacuum port on the canister lid of FIG. 17, with the inventive vacuum adapter fitting seating on the vacuum port to provide a vacuum seal.

A fail safe vacuum port fitting adapter 271 is illustrated in FIGS. 18 and 19. The adapter 271, which is preferably made of brass, has a tapered, ribbed frustoconical upper portion 272 which is adapted to receive and retain an open end of a vacuum line in a known manner. A central bore 273 extends through the upper portion 272 and connects with an inner tapered section 274 which is sized to seat over the vacuum port 254 in the lid 242, as shown in FIG. 18, such that a vacuum can be drawn within the canister 221. The adapter 271 includes a lower section 275 which is substantially cylindrical in shape and includes a pair of laterally extending through bores 281 which are preferably positioned opposite each other. The through bores 281 and the overall length of the adapter 271 insure that it will not seat on the other ports in the lid 242, such as the patient port 255, as shown in FIG. 19 and, thus, no vacuum can be inadvertently drawn on the canister 221 via any of the other lid ports.

X. Improved Drain Opening Stopper 241

FIG. 17 illustrates an improved container drain opening stopper 241 which includes a peripheral ridge 283 integrally molded therein. The ridge 283 acts as a positive O ring seal when the stopper 241 is positioned in the container drain opening 235 to prevent inadvertent leakage of fluid from the container 222.

XI. Single Use Flush Kit 290

FIG. 21 shows a single use disposable canister flush kit 290 for use with a reusable container such as the container 222. The reusable container 222 may be molded from, e.g., polycarbonate plastic, which is reusable and autoclavable up to 220 degrees F, or other materials, such as Radel plastic, which is autoclavable up to 321 degrees F. The kit 290 includes a single use lid 291, which is preferably constructed as described above with respect to lid 242. The single use lid 291 can be molded from, e.g., polystyrene plastic, which is not autoclavable and includes an integral Pour-X filter 292 positioned within the vacuum port 254. The kit 290 also includes a plurality of port covering caps 293 and an accessory port cap 294, each of which is attached by a respective plastic tether 295 in a spider-like fashion to a center ring 296. The ring 296 is preferably sized to slide down over the vacuum port 254 in the lid 291 and the tethers 295 extend outward at differing lengths and in differing directions such that the caps 293 and 294 are positioned to cover each of the patient port 255, the tandem port 256, the ortho port 257 and the accessory port 245. One tether 295a is long enough to be doubled backward so that the connected cap 293a covers the vacuum port 254. The kit 290 also includes a single use drain opening stopper 241 and a plunger rod 92, and, optionally, a single use flush jet adapter 252. Alternatively, the lid 292 can be made of autoclavable, reusable material and the kit 290 can include, instead, a single use Pour-X filter 292 which is insertable in the vacuum port 254.

XII. Modified Flush Jet Adapter 301

FIG. 22 illustrates a modified flush jet adapter 301 which is approximately twice the length of the adapter 252 described earlier. The modified adapter 301 includes a bottom opening 302 which connects with a tapered cavity 303 with a closed upper end 304 which is positioned to engage a top of the plunger rod 92 as the adapter 301 is inserted into the accessory port 245. The modified adapter 301 includes a centered, threaded inlet 305 for receiving a flush jet, which inlet 305 terminates in a well 311. The well 311 connects with an elongate spray cavity 312 which extends almost the length of the adapter 301 and connects with a plurality of outlet spray ports 313 which are spaced along the length of the cavity 312. With the multiple spray ports 313, spray can be directed into the container 222 in a number of streams simultaneously to multiply the cleansing action and to direct the spray to the optimum locations within the container 222. Research has shown that optimum cleaning action is achieved when ⅓ of the cleaning fluid stream is directed above the container ledge 226 and ⅔ of the stream is directed below the ledge 226. Although not illustrated in FIG. 22, the cavity 312 can change in diameter along its length, and the spray ports 313 can vary in size so that a predetermined optimum portion of the fluid stream is directed out of each spray port 313.

XIII. Modified Canister Flushing System 321 and Holding Tank

Figure 23:
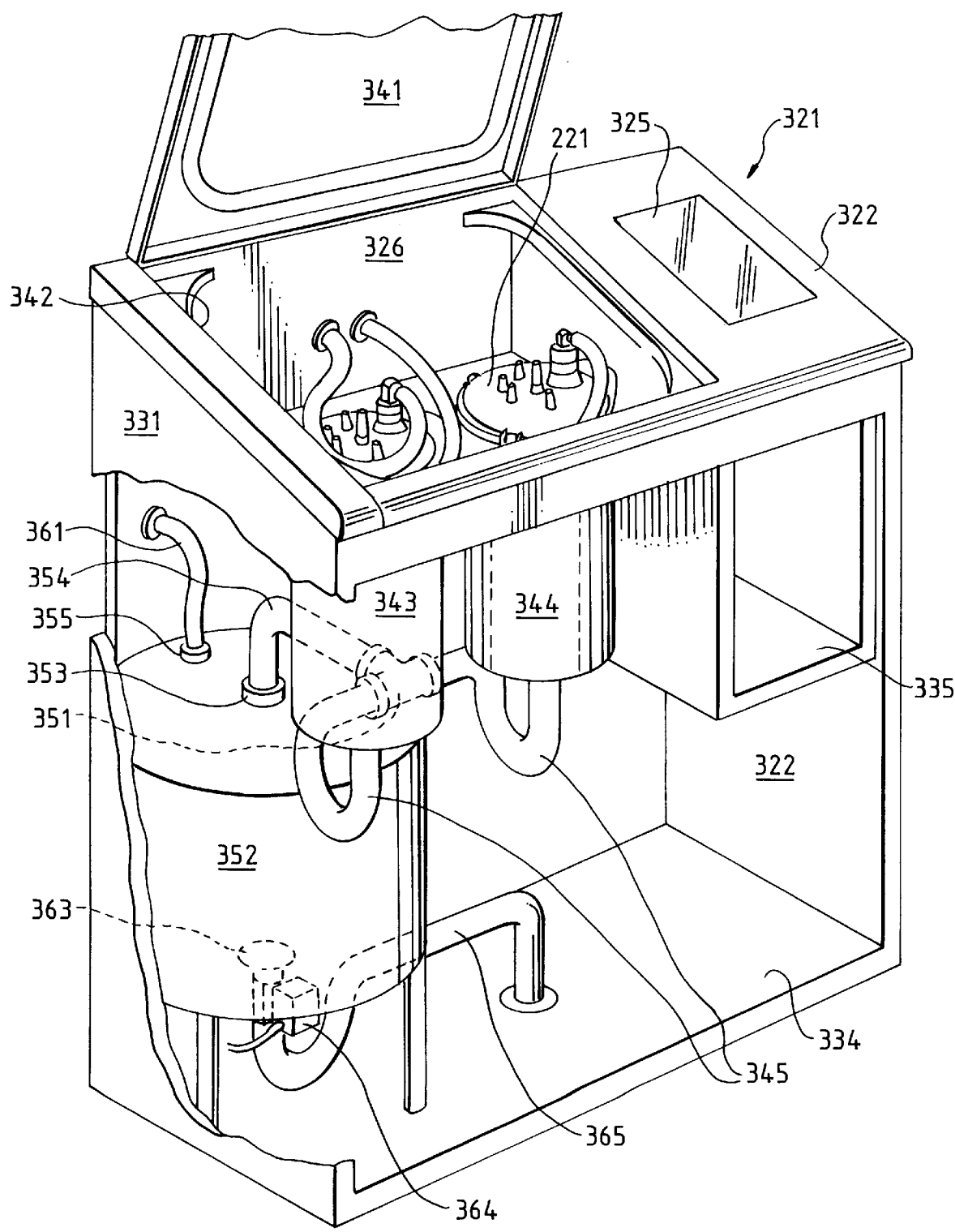
FIG. 23 is a perspective view of an alternative liquid medical waste disposal and canister flushing system embodying the present invention, with a holding tank connected to the subsink drains, with the holding tank having a top inlet for the optional introduction of a PH neutralizing solution and with a valved drain connecting the holding tank to a floor drain.

FIG. 23 illustrates a modified canister flushing system 321 which is illustrated for use with the canisters 221 described above. The flushing system 321 is similar in most respects to the system 2 of FIG. 1 and also includes a cabinet 322, a plumbing system 323 (FIG. 24) and a control system 324 (FIG. 25) controlled by a keyboard panel 325.

Figure 24:
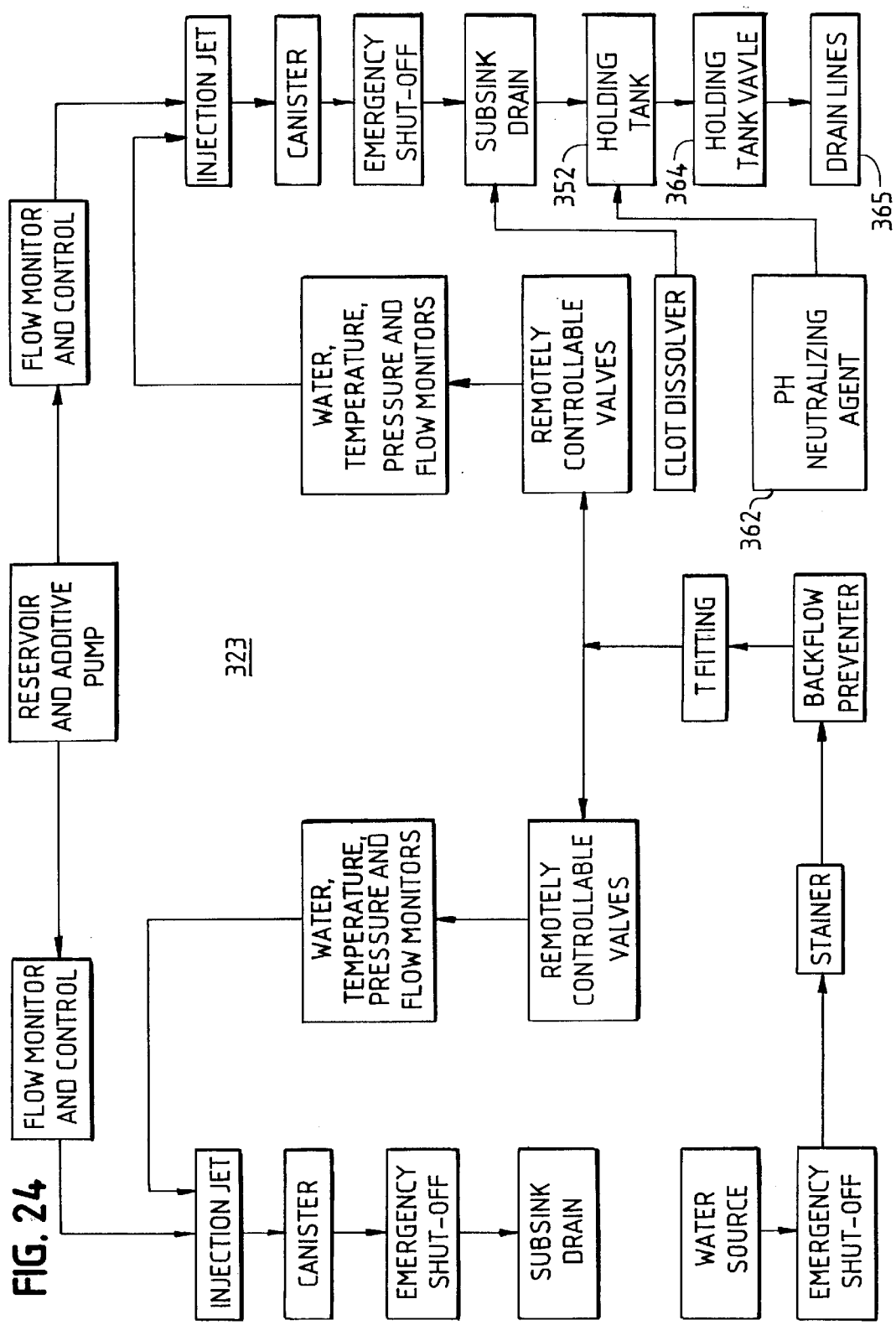
FIG. 24 is an alternative schematic plumbing diagram for the system of FIG. 23.

The cabinet 322 includes many of the same components as described earlier with respect to FIG. 1, including a back panel 326; first and second side panels 331 and 332 and a top 333. A removable front access panel is not shown, but it selectively covers a large opening 334 which houses the drain portion of the plumbing system 323 and a smaller opening 335 which houses the control system 324. A hinged lid 341 selectively covers a sink 342 from which a pair of subsinks 343 and 344 depend. Each subsink 343 and 344 is connected with a respective drain trap 345 which traps 345 are connected together via a plumbing Tee fitting 351. Here the system 321 differs from that of FIG. 1 in that a holding tank 352 has a first top inlet 353 which is connected to the Tee fitting 351 via an elbow 354 so that fluid draining from the subsinks 343 and 344 drain directly into the holding tank 352. The holding tank 352 has a second top inlet 355 which connects to a hose 361 which selectively feeds a ph neutralizing fluid from a source of ph neutralizer 362 (FIG. 24). The holding tank 352 has a bottom drain opening 363 with a remotely controlled drain outlet valve 364 such that the holding tank 352 can be selectively drained via a drain pipe 365 after a suitable neutralizing time-out cycle.

XIV. Plumbing Systems 8 and 323

Figure 7:
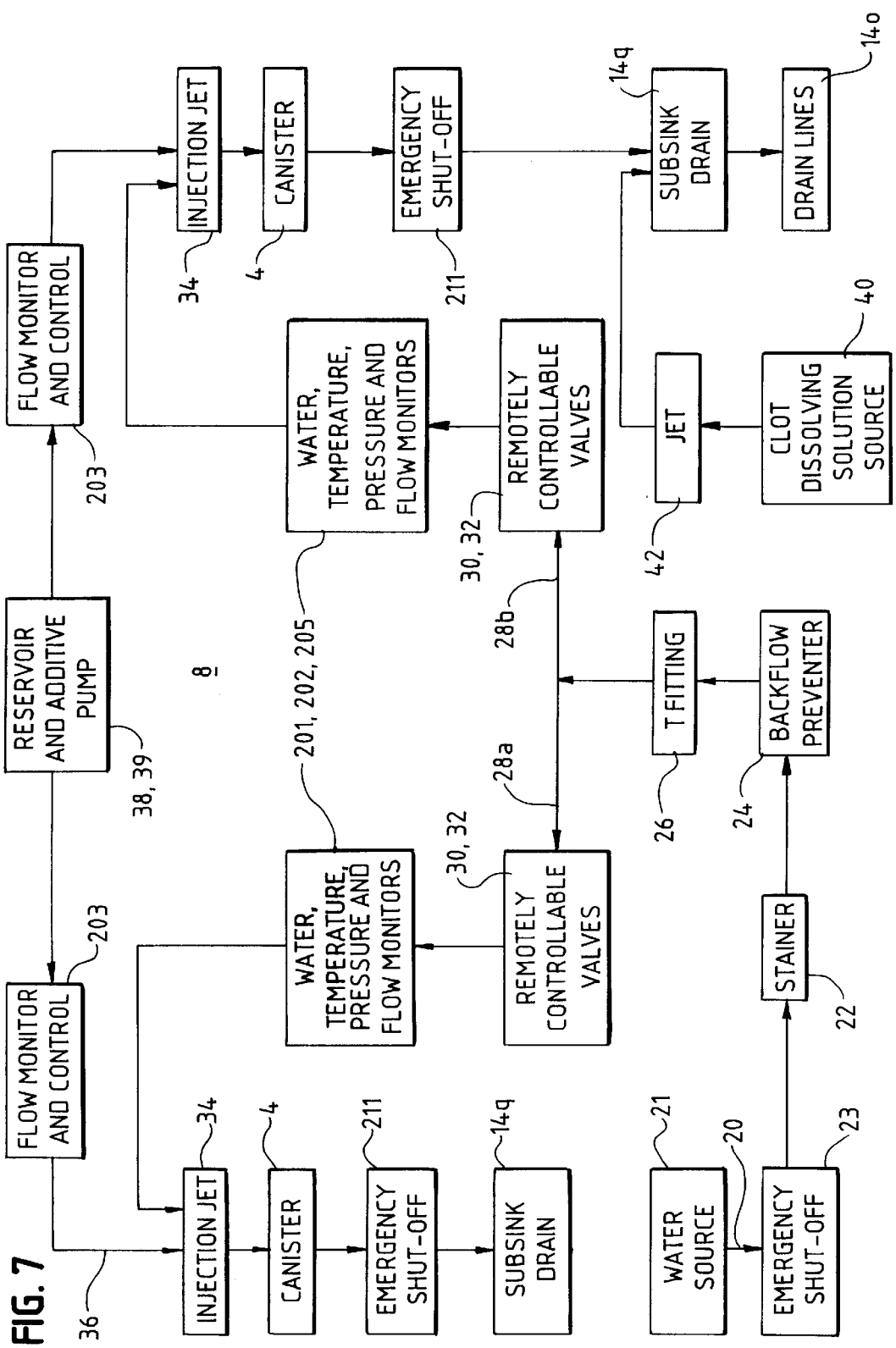
FIG. 7 is a schematic diagram of a plumbing system thereof.

The plumbing system 8 is illustrated in block diagram form in FIG. 7 and generally includes a supply subsystem 8a and a drain subsystem 8b. The supply subsystem 8a includes a water inlet line 20 connected to a suitable pressurized water source 21, such as the normal municipal water service, a water tank or a water pump. A strainer 22 is provided in the water inlet line 20 and a backflow preventer valve 24 is provided downstream therefrom. The water inlet line 20 connects to a T-fitting 26, forming first and second supply branches 28a,b.

Each supply subsystem branch 28a,b includes a gate-type shut-off valve 30 and a solenoid-actuated valve 32 in line therewith. Each water inlet line 20 terminates in an injection jet 34, which also communicates with a cleaning solution injection line 36 communicating with a cleaning solution source 38, which can include a pump 39 for pumping the cleaning solution under pressure to the injection jet 34.

Each injection jet 34 includes a generally cylindrical body 34a with a flanged upper end 34b and a lower end 34c. A jet passage 34d extends downwardly from a threaded water inlet port 34e located off-center in the upper end 34b. The water inlet line 20 is connected to the water inlet port 34e by an elbow 34k. A discharge orifice 34f is located in the body lower end 34c, and is also off-center whereby the jet passage 34d is skewed with respect to a longitudinal axis 34j of the injection jet body 34a. Due to the skewed, angular orientation of the jet passage 34d, diluted cleaning solution therefrom is directed generally at the container sidewall 4g, creating a swirling flushing action in the container 4b. A cleaning solution inlet port 34g is formed in the body upper end 34b and communicates with a cleaning solution passage 34h which forms a Y-intersection 34i with the jet passage 34d in an interior part of the body 34a. The cleaning solution inlet port 34g is connected to the cleaning solution line 36.

A venturi effect is created by passage of water through the jet passage 34d whereby cleaning solution is drawn through the cleaning solution passage 34h for combining with water to form the diluted cleaning solution mixture which is discharged through the discharge orifice 34f. Alternatively, cleaning solution can be pumped under pressure via pump 39 into the injection jet 34 or 252 such that no venturi effect is needed to draw cleaning solution in with the water.

An optional clot-dissolving solution source 40 communicates with a drain line jet 42 directed into the drain line 14o and functions to dissolve blood clots therein. Although the clot-dissolving solution source 40 and the jet 42 are optionally shown on the second plumbing system branch 28b, they could be provided on the first branch 28a as well, or eliminated all together whereby clots in the drain line 14o could be dealt with manually.

The plumbing system 323 is illustrated in FIG. 24, and includes each of the elements described above with respect to FIG. 7. In addition, the holding tank 352 is shown schematically along with the holding tank drain outlet valve 364 and the ph neutralizing fluid source 362.

XV. Control Systems 10 and 324

The control system 10 is illustrated in block diagram form in FIG. 8 and utilizes a control microprocessor 50. A program port 52 provides input access to the microprocessor 50 through a suitable RAM device 53a. A ROM device 54 is also connected to the microprocessor 50.

Analog-to-digital input conversion capabilities are provided by an A\D convertor 56 which is connected to an encoder 58, which in turn is connected to the microprocessor 50 through a RAM device 53b. A selection key 60 also provides digital input to the encoder 58. A level probe 62 is connected to the solution source 38 for monitoring the level therein and is connected to the RAM device 53b through an amplifier 62a.

A solenoid valve control 64 includes a digital output module 64a which is connected to the solenoid valves 32 and to a pair of indicator lights 64b for indicating the open or closed positions of the solenoid valves 32. The digital output module 64a is connected to the microprocessor 50 through a RAM device 53c.

A display device 66 is mounted on the cabinet top panel 14e and is connected to the microprocessor 50 through a RAM device 53d and a driver 66a and can comprise, for example, an LED or LCD display for indicating the state of the control system 10 or various functions thereof, such as time remaining to complete a flush cycle, delay mode (as explained in more detail below), etc.

A voice enunciation subsystem 68 includes a speech synthesizer 68a connected to the microprocessor 50, a RAM device 53e, a speech ROM device 68b, an amplifier 68d and a suitable output device, such as a speaker 68e, all suitably interconnected as shown in FIG. 8. A water pressure sensor 201 is connected to the microprocessor 50 for monitoring water pressure to insure that it is adequate. A water flow sensor 202 and an additive flow sensor 203 monitor fluid flow to allow titration of the additive and flow of water to be monitored to calculate concentration of additive (cleaning solution) in the water. The microprocessor 50 thus controls valves 32 and the pump 39 to achieve the desired additive concentration. Monitoring of water flow by the microprocessor 50 insures compliance with government regulations. A water temperature monitor 205 allows the microprocessor 50 to monitoring of water temperature. A remotely controlled emergency shut-off 23 and 211 allows the microprocessor 50 to shut off the drain of the cabinet 6 as well as all fluid inputs in the event that monitored parameters are outside of predetermined limits. The microprocessor 50 also stores and archives of any exceptions to desired parameters. An optional modem 212 can be provided for remote monitoring and emergency paging functions for the on-board display 66 can be provided for instantaneous feedback of system conditions.

Figure 25:
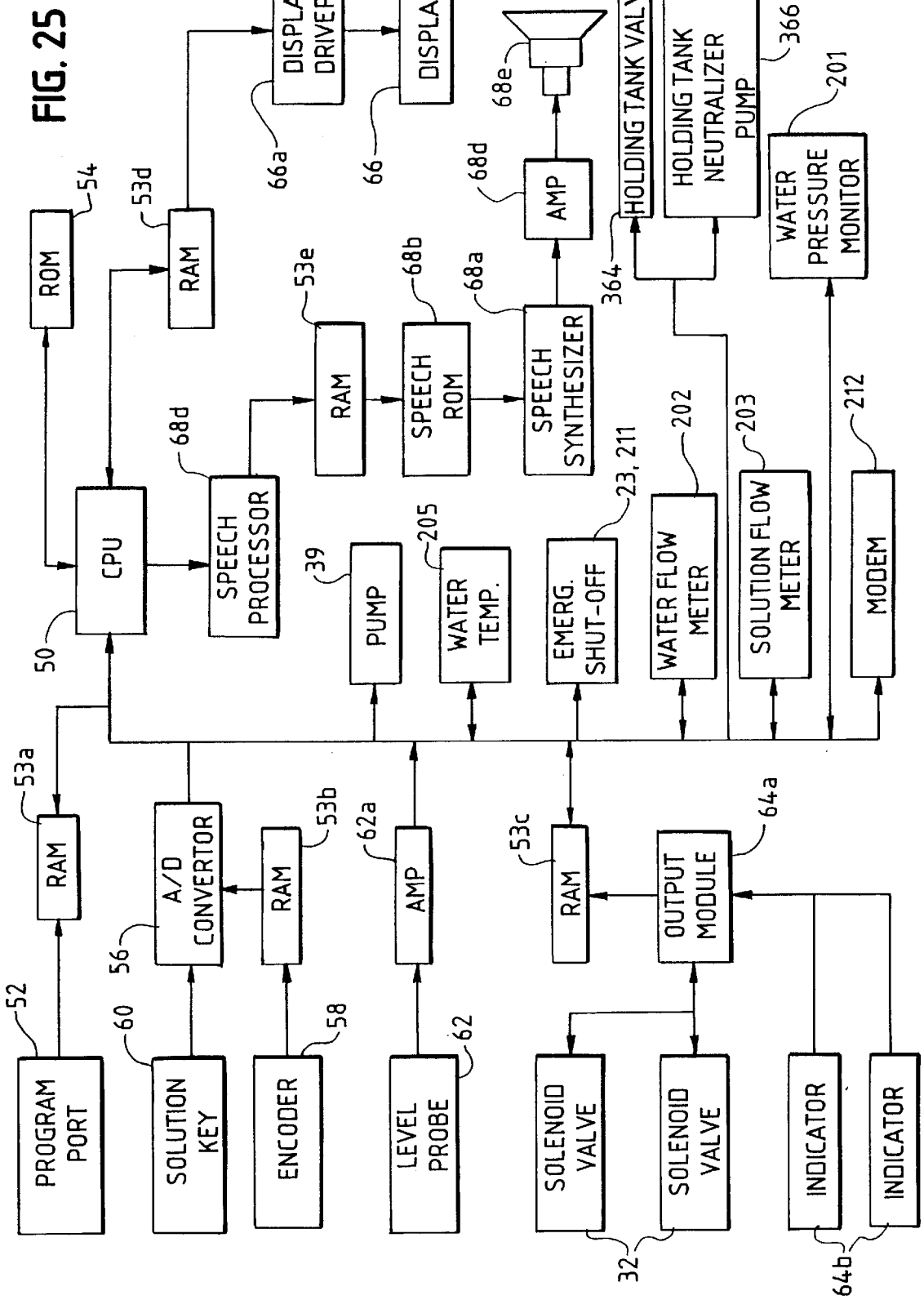
FIG. 25 is an alternative schematic diagram of a control system for the system of FIG. 23.

The plumbing system 324 is illustrated in FIG. 25, and includes each of the elements described above with respect to FIG. 8. In addition, the holding tank drain outlet valve 364 and a pump 366 for pumping fluid into the holding tank 352 from the ph neutralizing fluid source 362 are shown as being controlled by the microprocessor 50.

It will be appreciated that the control system 10 can comprise various alternative configurations with appropriate analog, digital or analog/digital components for controlling various functions of the system 2. In particular, other inputs and outputs could be provided for monitoring various functions of the system 2 and for automating same to a greater or lesser degree.

XVI. Operation and Liquid Medical Waste Disposal and Canister Flushing Method

Figure 9:
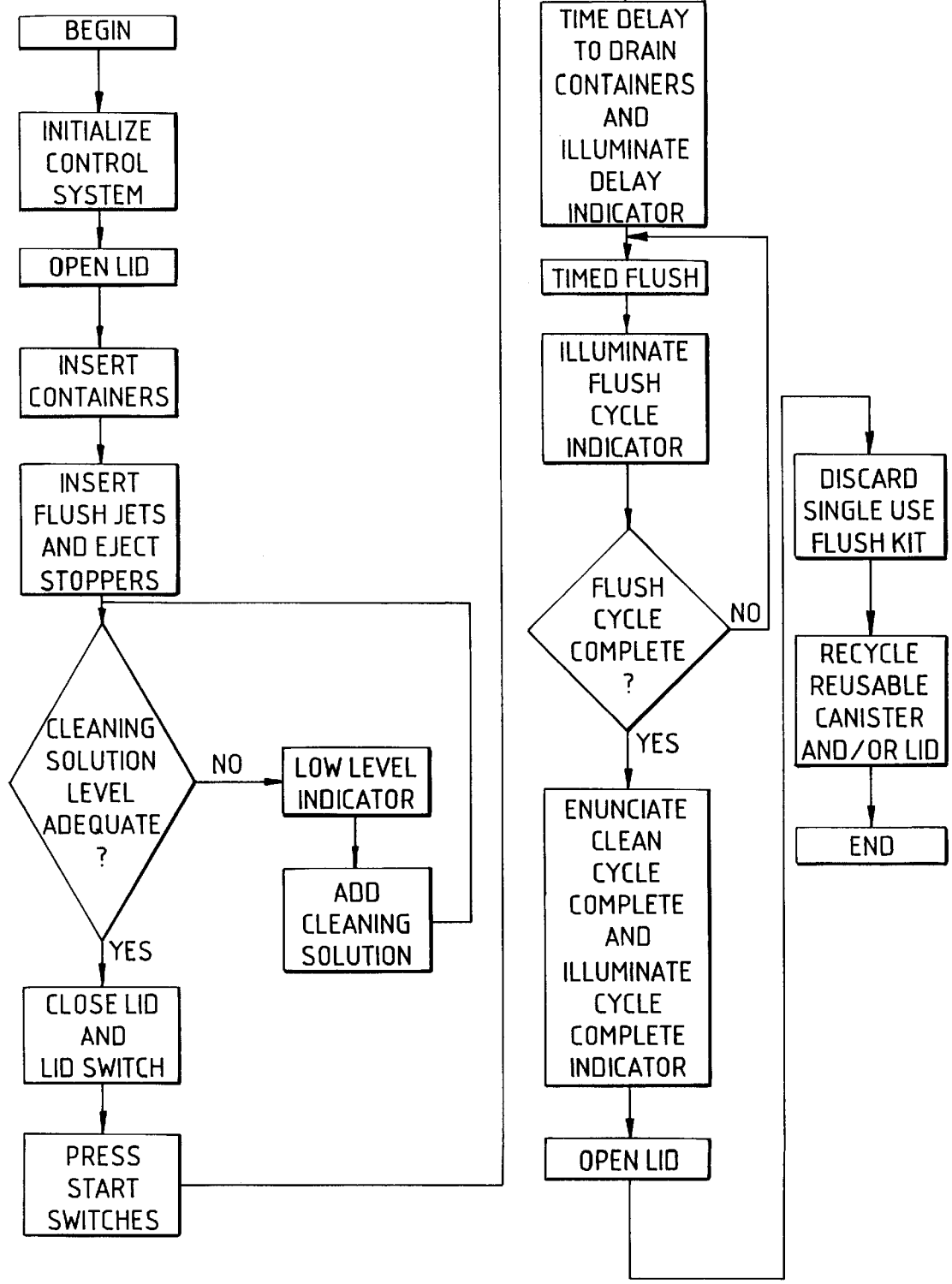
FIG. 9 is a flow chart of a method of liquid waste disposal and canister flushing embodying the present invention.

FIG. 9 comprises a flow chart showing a method of disposing of liquid medical waste and flushing the containers 4. While the following description is directed to the canister and subsink embodiments illustrated in FIGS. 1–7, the steps are equally applicable to the alternative embodiments illustrated in FIGS. 10–15.

The control system 10 is initialized, for example, by programming the microprocessor 50 with appropriate operating parameters including delay or drain cycle times, flush cycle times, etc. The cabinet lid 14j is opened to access the sink 14k. One or two canisters 4 are placed in respective subsinks 14l, which have circular mouths 14m with diameters intermediate the diameters of the canister lids 4c and bases 4f whereby the containers 4 extend partway into the subsinks 14l and the container sidewalls 4g form friction fits with the subsink mouths 14m whereby a friction seal is formed around the circumference of the container sidewalls 4g.

The injection jets 34 are next connected by removing the caps 12f from the plunger subassemblies 12 to provide access to the container lid accessory ports 4d wherein the injection jet body lower ends 34c engage the plunger rod upper ends 12e. Pushing the injection jet bodies 34a into the container lid accessory ports 4d dislodges the plunger stoppers 12d from the container base drain openings 12a whereby the containers 4 drain their contents into the subsinks 14l. The cabinet subsink drain openings 14q are sized larger with diameters D1 than the container base accessory ports 12a with diameters D2 whereby the liquid medical waste from the containers 4 is substantially instantly drained from the subsinks 14l. In other words, the subsinks 14l have greater flow discharge rate capacities than the containers 4 whereby backing up of medical waste within the subsinks 14l is avoided.

With the injection jets 34 placed in the container lid accessory ports 4d, the cabinet lid 14j can be closed, which permits the flush cycles to be commenced or initiated by pressing the start buttons. The cabinet lid 14j can be positioned sufficiently close to the injection jets 34 that the latter are retained in place in the container lid accessory ports 4d by the cabinet lid 14j during the flush cycle. A timed delay of the commencement of the flush cycle is provided after the cabinet lid 14j is closed and the start buttons are actuated, which delay permits substantially complete drainage of the containers 4 through the subsinks 14l before the flush cycle commences. Thus, the flush cycle is initiated in substantially empty containers 4. The microprocessor 50 can be programmable to vary the timed delay for canister draining and for the length of the flush cycle.

As a general guideline, it is desirable to flush the containers 4 with a volume of solution equal to approximately 3 to 4 times their capacities. The cleaning solution mixture preferably comprises water and a suitable agent for killing virus and bacteria. For example, sodium hypochlorite (i.e., bleach) in a solution of about 1200 to 1400 parts per million with water has generally been found to be suitable. A delay of approximately 8 seconds has been found to be sufficient to drain the containers 4, and a flush cycle of approximately 45 seconds has generally been found to be sufficient.

The solution mixture is preferably chosen to meet the particular objectives of a disposal and flushing system. For example, disinfection and flushing are generally the primary objectives with liquid medical waste containers 4, which for most reuse purposes do not have to be cleaned to the point where they would be considered sterile, since sterility is normally not required for liquid medical waste canisters. The plunger subassemblies 12 and the container lids 4c can be disposed of and the container bodies 4a reused at a fraction of the cost of disposing of complete containers 4 full of liquid medical waste. The lids 4c and the plunger subassemblies 12 would generally be considered "white" trash in medical facilities due to relatively low concentrations of liquid medical waste thereon and thus would not be subjected to the more stringent requirements typically in place for handling and disposing of the actual liquid medical wastes.

The flushed liquid medical waste from the system 2 would mix with the effluent from the medical facility in its plumbing drainage system and could normally be discharged into a municipal sewer system at levels well below the maximums permitted for medical waste effluents.

Figure 26:
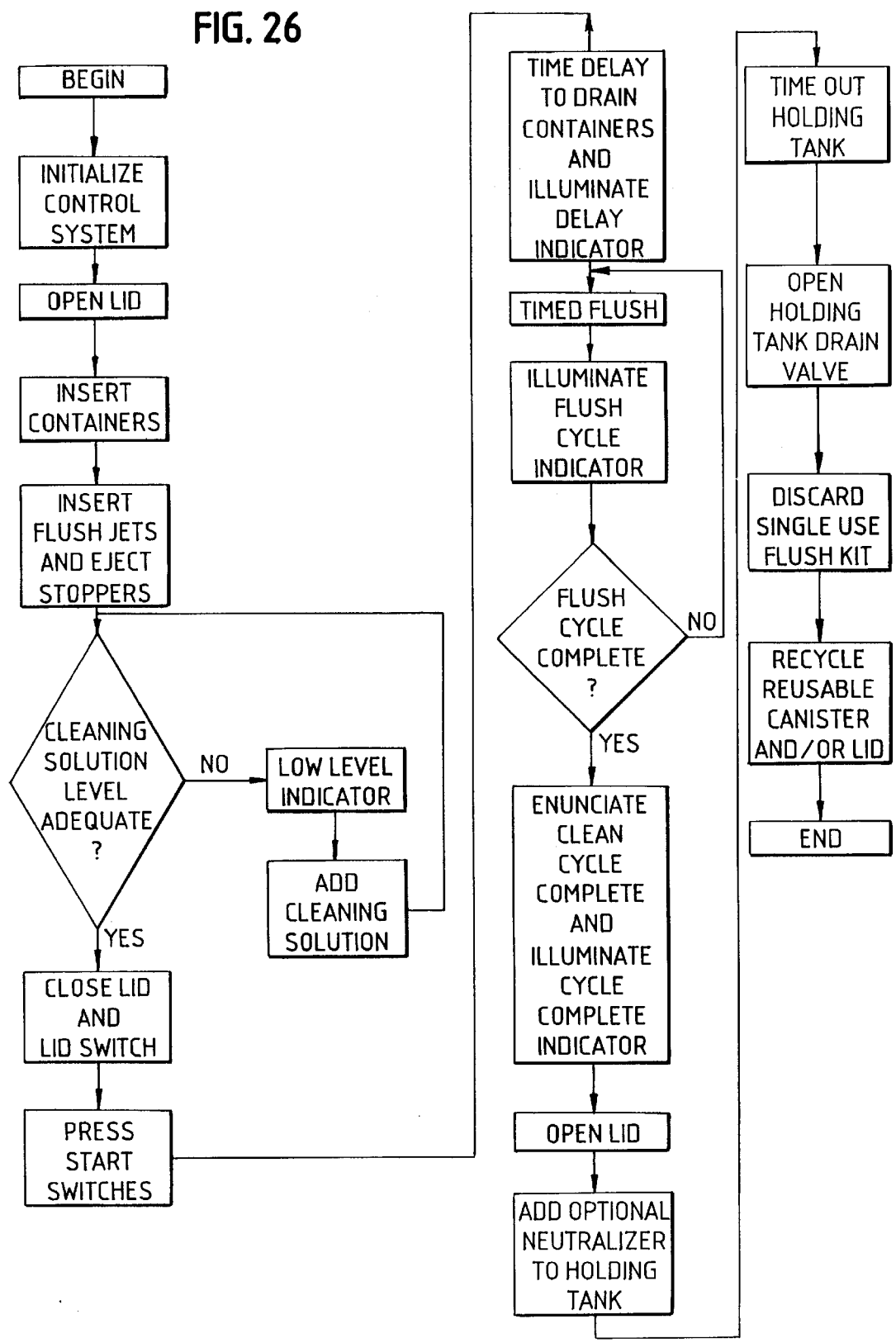
FIG. 26 is an alternative flow chart of a method of liquid waste disposal and canister flushing for the system of FIG. 23.

FIG. 26 illustrates an alternative method of disposing of liquid medical waste and flushing canisters, with the following description being directed to the alternative system with holding tank 352 illustrated in FIG. 23. The method of FIG. 26 is similar in most respects to the method of FIG. 9 with the exception of the last five steps. Cleaning fluid from the subsinks 343 and 344 is drained directly into the holding tank 352 and the microprocessor 50 is, optionally, programmed to add a preset amount of a ph neutralizing solution to the holding tank 352. The holding tank fluid dwell time is then timed and the holding tank drain outlet valve 364 is then opened to allow effluent from the holding tank 352. The single use kit is then discarded as "white trash", the reusable canister 4, 222, etc. is recycled by autoclaving or dishwashing.

It is to be understood that while certain forms of the present invention have been illustrated and described herein, it is not to be limited to the specific forms or arrangement of parts described and shown.

We claim:

1. A canister usable with a liquid waste disposal and canister flushing system, said flushing system including a source of cleaning fluid under pressure and a cabinet including a subsink, said canister comprising:
   (a) a container with an open top and a closed bottom portion which is insertable in said subsink, a drain opening formed in said closed bottom, said container also including a peripheral flange extending outwardly from said open top; and
   (b) a lid removably attachable to the open top of said container in covering relation with said open top, said lid including an accessory port sized to accommodate a flush jet and having an outwardly extending peripheral receiver portion which is shaped and sized to mate with the peripheral flange on the container such that said accessory port is aligned with said drain opening when said lid is attached to said container.

2. A canister as in claim 1, and further comprising:
   (a) a slot formed in said container peripheral flange; and
   (b) a tab formed in said lid peripheral receiver portion, said tab being positioned such that it engages said slot when the lid is correctly oriented on the container.

3. A canister as in claim 1, and further comprising:
   (a) a flush jet adapter including a fluid passage and a jet port, said adapter including an elongate body with a longitudinal slot formed therein; and wherein
   (b) said accessory port in said lid has an open top and includes an accessory tab extending inward into said accessory port, said slot on said flush jet adapter mating with said accessory tab when said flush jet adapter is inserted into said accessory port such that said jet port is correctly positioned to direct a cleaning jet into said container for optimum cleaning effect.

4. A canister as in claim 1, and further comprising a flush jet adapter including:
   (a) an elongate body;
   (b) a bottom opening in said elongate body which bottom opening connects with a tapered internal cavity having a closed upper end; and
   (c) a threaded inlet for receiving a flush jet, which inlet connects with an internal elongate spray cavity which extends almost the length of the adapter body and connects with a plurality of outlet jet ports which are spaced along the length of the spray cavity.

5. A canister as in claim 1, and further comprising:
   (a) a stopper positioned in said container drain opening; and
   (b) a plunger rod positioned within said container, said plunger rod having one end in contact with said stopper and a second end extending upward into said accessory port, said plunger rod being engageable by said flush jet adapter when it is inserted into said accessory port such that said plunger rod is forced downward, thus forcing said stopper out of said drain opening when said plunger rod is forced downward by said flush jet.

6. A canister as in claim 5, wherein:
   (a) said stopper includes a peripheral ridge molded therein which ridge serves to form an O ring seal between said stopper and said container drain opening.

7. A canister as in claim 1, and further comprising:
   (a) a rim extending at least partially around said open top of said container; and
   (b) a plurality of resilient tabs formed and being spaced around the periphery of said lid, said resilient tabs engaging said container rim to lock said lid onto said container such that release of said lid requires at least three of said tabs to be released from said rim.

8. A canister as in claim 1, wherein:
   (a) said container closed bottom is radiused downward from an outside periphery to a center portion thereof; and
   (b) a plurality of feet extend downward from said bottom to provide a stable platform for said container.

9. A canister as in claim 1, and further comprising:
   (a) a tapered vacuum port and at least one non-vacuum port formed in said lid, said vacuum port being taller than said non-vacuum port; and
   (b) a fail safe vacuum port fitting adapter including:
      (i) a tapered, ribbed upper portion which is sized to receive and retain an open end of a vacuum line;
      (ii) a central bore extending through the upper portion and connecting with an inner tapered section which is sized to seat over the tapered vacuum port such that a vacuum can be drawn within the canister; and
      (iii) a lower section extending below the inner tapered section, said lower section including at least one through bore connecting with said inner tapered section, said lower section having a length such that, when said vacuum fitting adapter is inadvertently placed over said non-vacuum port, a bottom of said vacuum port fitting adapter rests on an upper surface of said lid to hold said inner tapered section above said non-vacuum port to prevent a vacuum from being drawn on said container via said non-vacuum port.

10. A canister usable with a liquid waste disposal and canister flushing system, said flushing system including a source of cleaning fluid under pressure and a cabinet including a subsink, said canister comprising:
    (a) a container with an open top and a closed bottom portion which is insertable in said subsink, a drain opening formed in said closed bottom;
    (b) a lid removably attachable to the open top of said container in covering relation with said open top, said lid including an accessory port sized to accommodate a flush jet adapter;
    (c) a flush jet adapter including a fluid passage and at least one jet port, said adapter including an elongate body with a longitudinal slot formed therein; and wherein
    (d) said accessory port in said lid has an open top and includes an accessory tab extending inward into said accessory port, said slot on said flush jet adapter mating with said accessory tab when said flush jet adapter is inserted into said accessory port such that said jet port is correctly positioned to direct a cleaning jet into said container for optimum cleaning effect.

11. A canister as in claim 10, wherein:
(a) said container includes a peripheral flange extending outwardly from said open top and a slot formed in said container peripheral flange; and
(b) said lid includes an outwardly extending peripheral receiver portion which is shaped and sized to mate with the peripheral flange on the container such that said accessory port is aligned with said drain opening when said lid is attached to said container and a tab formed in said lid peripheral receiver portion, said tab being positioned such that it engages said slot when the lid is correctly oriented on the container.

12. A canister as in claim 10, said flush jet adapter including:
(a) an elongate body;
(b) a bottom opening in said elongate body which bottom opening connects with a tapered internal cavity having a closed upper end; and
(c) a threaded inlet for receiving a flush jet, which inlet connects with an internal elongate spray cavity which extends almost the length of the adapter body and connects with a plurality of jet ports which are spaced along the length of the spray cavity.

13. A canister as in claim 10, and further comprising:
(a) a stopper positioned in said container drain opening; and
(b) a plunger rod positioned within said container, said plunger rod having one end in contact with said stopper and a second end extending upward into said accessory port, said plunger rod being engageable by said flush jet adapter when it is inserted into said accessory port such that said plunger rod is forced downward, thus forcing said stopper out of said drain opening when said plunger rod is forced downward by said flush jet.

14. A canister as in claim 13, wherein:
(a) said stopper includes a peripheral ridge molded therein which ridge serves to form an O ring seal between said stopper and said container drain opening.

15. A canister as in claim 10, and further comprising:
(a) a rim extending at least partially around said open top of said container; and
(b) a plurality of resilient tabs formed and being spaced around the periphery of said lid, said resilient tabs engaging said container rim to lock said lid onto said container such that release of said lid requires at least three of said tabs to be released from said rim.

16. A canister as in claim 10, wherein:
(a) said container closed bottom is radiused downward from an outside periphery to a center portion thereof; and
(b) a plurality of feet extend downward from said bottom to provide a stable platform for said container.

17. A canister as in claim 10, and further comprising:
(a) a tapered vacuum port and at least one non-vacuum port formed in said lid, said vacuum port being taller than said non-vacuum port; and (b) a fail safe vacuum port fitting adapter including:
(i) a tapered, ribbed upper portion which is sized to receive and retain an open end of a vacuum line;
(ii) a central bore extending through the upper portion and connecting with an inner tapered section which is sized to seat over the tapered vacuum port such that a vacuum can be drawn within the canister; and
(iii) a lower section extending below the inner tapered section, said lower section including at least one through bore connecting with said inner tapered section, said lower section having a length such that, when said vacuum fitting adapter is inadvertently placed over said non-vacuum port, a bottom of said vacuum port fitting adapter rests on an upper surface of said lid to hold said inner tapered section above said non-vacuum port to prevent a vacuum from being drawn on said container via said non-vacuum port.

18. A liquid waste disposal and canister flushing system, said flushing system including:
(a) a flush jet adapter attached to a source of water and a source of cleaning solution;
(b) a canister to be flushed, said canister including a lid with an upper accessory port which accommodates the insertion of said flush jet adapter and a drain opening for draining the contents of said canister;
(c) a cabinet including a sink with a floor;
(d) a subsink which is sized to hold the canister during flushing, said subsink including a basin with a bottom surface which extends below the floor of said cabinet with a subsink drain opening in said basin bottom surface;
(e) a holding tank with an inlet connecting said subsink drain opening such that the contents of said subsink drain into said holding tank; and
(f) said holding tank includes a drain opening which connects to a sewer system for draining the holding tank into said sewer system.

19. A liquid waste disposal and canister flushing system as in claim 18, wherein said canister further comprises:
(a) a stopper extending into said canister drain opening; and
(b) a plunger rod which is positioned within said canister and extends upward into said accessory port, said plunger rod being engageable by said flush jet adapter when it is inserted into said accessory port such that said plunger rod is forced downward, thus forcing said stopper out of said canister drain opening.

20. A liquid waste disposal and canister flushing system as in claim 18, and further comprising:
(a) a source of ph neutralizing solution; and
(b) said holding tank includes an additional inlet connected to said source of ph neutralizing solution.

21. A liquid waste disposal and canister flushing system as in claim 18, and further comprising:
(a) a remotely controlled valve connected to selectively close or open said holding tank drain opening.

* * * * *